（12） United States Patent
Beall et al.

US007507789B2

(10) Patent No.: US 7,507,789 B2
(45) Date of Patent: Mar. 24, 2009

(54) DETECTION OF *ANAPLASMA PLATYS*

(75) Inventors: Melissa Jane Beall, Yarmouth, ME (US); Phyllis Ione Tyrrell, Yarmouth, ME (US); Ramaswamy Chandrashekar, Scarborough, ME (US); Jiayou Liu, Scarborough, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 0 days.

(21) Appl. No.: 11/697,769

(22) Filed: Apr. 9, 2007

(65) Prior Publication Data

US 2008/0248497 A1    Oct. 9, 2008

(51) Int. Cl.
    C07K 14/005    (2006.01)
    G01N 33/569    (2006.01)
    G01N 33/566    (2006.01)
    C07H 21/04     (2006.01)

(52) U.S. Cl. ............... 530/300; 435/7.22; 536/23.1; 436/501

(58) Field of Classification Search ............ 424/234.1, 424/184.1, 282.2; 530/350, 825, 300; 435/69.1, 435/366, 7.1, 7.32, 7.22; 514/2; 536/23.1; 436/501
See application file for complete search history.

(56) References Cited

U.S. PATENT DOCUMENTS

| | | | |
|---|---|---|---|
| 5,192,679 | A | 3/1993 | Dawson et al. |
| 5,401,656 | A | 3/1995 | Dawson et al. |
| 5,413,931 | A | 5/1995 | Dawson et al. |
| 5,726,010 | A | 3/1998 | Clark |
| 5,789,176 | A | 8/1998 | Dawson et al. |
| 5,869,335 | A | 2/1999 | Munderloh et al. |
| 5,928,879 | A | 7/1999 | Dumler et al. |
| 5,955,359 | A | 9/1999 | Dumler et al. |
| 5,976,791 | A | 11/1999 | Mabilat et al. |
| 5,989,848 | A | 11/1999 | Dawson |
| 6,015,691 | A | 1/2000 | Walker et al. |
| 6,025,338 | A | 2/2000 | Barbet et al. |
| 6,034,085 | A | 3/2000 | Joshi et al. |
| 6,204,252 | B1 | 3/2001 | Murphy et al. |
| 6,207,169 | B1 | 3/2001 | Reed et al. |
| 6,231,869 | B1 | 5/2001 | Reed et al. |
| 6,277,381 | B1 | 8/2001 | Reed et al. |
| 6,284,238 | B1 | 9/2001 | Coughlin et al. |
| 6,306,402 | B1 | 10/2001 | Reed et al. |
| 9,306,394 | | 10/2001 | Murphy et al. |
| 6,355,777 | B1 | 3/2002 | Walker et al. |
| 6,392,023 | B1 | 5/2002 | Walker et al. |
| 6,403,780 | B1 | 6/2002 | Walker et al. |
| 6,458,942 | B1 | 10/2002 | Walker et al. |
| 2002/0064531 | A1 | 5/2002 | Walker et al. |
| 2002/0064535 | A1 | 5/2002 | Reed et al. |
| 2002/0068343 | A1 | 6/2002 | Reed et al. |
| 2002/0086984 | A1 | 7/2002 | Reed et al. |
| 2002/0115840 | A1 | 8/2002 | Walker et al. |
| 2002/0132789 | A1 | 9/2002 | Barbet et al. |

FOREIGN PATENT DOCUMENTS

| | | |
|---|---|---|
| WO | WO 9849312 A2 * | 5/1998 |
| WO | WO 98/42740 | 10/1998 |
| WO | WO 98/49313 | 11/1998 |
| WO | WO 99/13720 | 3/1999 |
| WO | WO 99/52370 | 10/1999 |
| WO | WO0000615 A2 * | 6/2000 |
| WO | WO 01/85949 A2 | 11/2001 |
| WO | WO 03/087758 | 10/2003 |

OTHER PUBLICATIONS

Bowie et al (Science, 1990, 257:1306-1310.*
Herbert et al (The Dictionary of Immunology, Academic Press, 3rd Edition, London, 1985, pp. 58-59.*
Roitt et al (Immunology, 1993, Mosby, St. Louis, p. 7.7-7.8.*
Holmes (Exp. Opin.Invest. Drugs, 2001, 10(3):511-519.*
Coleman et al. (Research in Immunology, 1994; 145(1): 33-36).*
Abaza et al. (Journal of Protein Chemistry, vol. 11, No. 5, 1992, pp. 433-444.*
Accession No. AAW81984; ADE36035; AC AAY78525.*
Lederman et al (Molecular Immunology 28:1171-1181, 1991).*
Li et al (Proc. Natl. Acad. Sci. USA 77:3211-3214, 1980).*
McBride, et al., "Molecular Cloning of the Gene for a Conserved Major Immunoreactive 28-Kilodalton Protein of *Ehrlichia canis*: a Potential Serodiagnostic Antigen", Clinical and Diagnostic Laboratory Immunology, 6:392-399 (1999).
McBride, et al., "A Conserved, Transcriptionally Action p28 Multigene Locus of *Ehrlichia canis*", Gene 254:245-252 (2000).
Murphy, et al., "Major antigenic proteins of the agent of human granulocytic ehrlichiosis are encoded by members of a multigene family", Infection and Immunity, 66(8):3711-3781 (1998).
Ohashi, et al., "Cloning and Characterization of Multigenes Encoding the Immunodominant 30-Kilodalton Major Outer Membrane Proteins of *Ehrlichia canis* and Application of the Recombinant Protein for Serodiagnosis", Journal of Clinical Microbiology, 36:2671-2680.
Ohashi, et al., "Immunodominant Major Outer Membrane Proteins of *Ehrlichia chaffeensis* are Encoded by a Polymorphic Multigene Family", Infection and Immunity, 66:132-139 (1998).
Suksawat, et al., "Seroprevalence of *Ehrlichia canis*, *Ehrlichia equi* and *Ehrlichia risticii* in sick dogs from North Carolina and Virginia", Journal Vet. Med. 14:50 (2000).

OTHER PUBLICATIONS

Yu, et al., "Comparison of *Ehrlichia chaffeensis* Recombinant Proteins for Serologic Diagnosis of Human Monocytotropic Ehrlichiosis" Journal of Clinical Microbiology, 37:2568-2575 (1999).

(Continued)

*Primary Examiner*—Shanon A. Foley
*Assistant Examiner*—Padma V Baskar
(74) *Attorney, Agent, or Firm*—McDonnell Boehnen; Hulbert & Berghoff LLP

(57) ABSTRACT

The invention provides compositions and methods for the detection of *Anaplasma platys* polynucleotides and polypeptides.

8 Claims, 6 Drawing Sheets

OTHER PUBLICATIONS

Yu, et al., "Genetic Diversity of the 28-Kilodalton Outer Membrane Protein Gene in Human Isolates of *Ehrlichia chaffeensis*" Journal of Clinical Microbiology, 37-1137-1143 (1993).

Yu, et al., "Characterization of the Complete Transcriptionally Active *Ehrlichia chaffeensis* 28 kDa Outer Membrane Protein Multigene Family" Gene 248:59-68 (2000).
Asanovich, KM, et al., "Particial Characterization of Cloned Genes Encoding Immunoreactive Proteins of *Ehrlichia equi* and the agent of Human Granulocytic Ehrlichiosis", 1996. Ab. Gen. Meet. American Society of Microbiology, Abstract No. D-22, p. 245.
Lodes, MJ, et al., "Serodiagnosis of Human Granulocytic Ehrlichiosis by using Novel Combinations of Immunoreactive Recombinant Proteins", 2001 Journal of Clinical Microbiology, vol. 39, No. 7, pp. 2471-2473.
Wormser, GP, et al., "False-Positive Lyme Disease Serology in Human Granulocytic Ehrlichiosis", 1996, Lancet, 347, pp. 981-982.
Magnarelli, LA, "Coexistence of Antibodies to tick-Borne Pathogens of Babesiosis, Ehrlichiosis and Lyme Borrelliosis in Human Sera", 1995, Journal of Clinical Microbiology, vol. 33, No. 11, pp. 3054-3057.
"Notification List—Notification that new names and new combinations have appeared in vol. 51, part 6 of the IJSEM", 2002, 52, 5-6, International Journal of Systematic and Evolutionary Microbiology.
International Search Report dated Sep. 17, 1993 for PCT/US03/10131.
GenBank Accession No. ABA26590 dated Mar. 24, 2006.
International Search Report dated Aug. 14, 2008 for PCT/US08/058842.
Uniprot Accession No. A0EWB2 dated Nov. 28, 2006.
Uniprot Accession No. Q3L6L0 dated Nov. 8, 2005.
Uniprot Accession No. Q2QFA4 dated Jan. 24, 2006.
Wang, et al., "Two Monoclonal Antibodies with Defined Epitopes of P44 Major Surface Proteins Neutralize *Anaplasma phagocytophilum* by Distinct Mechanisms", Infection and Immunity, vol. 74, No. 3, p. 1873-1882 (2006).
Anonymous, "*Anaplasma phagocytophilum* questions", Internet article (online), Oct. 17, 2006.
Simpson and Gaunt, "Immunocytochemical detection of *Ehrlichia platys* antigens in canine blood platelets", J. Vet. Diagn. Invest. 3:228-231 (1991).

* cited by examiner

Figure 1A

```
Apl_p44-1    TATTTTTATG TTGGTYTGGA YTATWGCCCG GCGTTTAGTA AGATAAATGG
Apl_p44-2    TATTTTTATG TTGGTTTGGA TTATTGCCCG GCGTTTAGTA AGATAAATGG
Apl_p44-3    TATTTTTATG TTGGTTTAGA TTATAGTCCG GCGTTTAGTA AGATAAATGG

Apl_p44-1    GTTTGAGATA AGAGAGAGTA CCGGGGAAAC TGCGGCAGTA TATCCGTACA
Apl_p44-2    GTTTGAGATA AGAGAGAGTA CCGGGGAAAC TGCGGCAGTA TATCCGTACA
Apl_p44-3    GTTTGAGATA AGAGAGAGTA CCGGGGAAAC TGCGGCAGTA TATCCGTACA

Apl_p44-1    TGAAAGATGG AACTAGAGTG GAGTGGAAAG CTGAGAAGTT CGACTGGAAC
Apl_p44-2    TGAAAGATGG AACTAGAGTG GAGTGGAAAG CTGAGAAGTT CGACTGGAAC
Apl_p44-3    TGAAAGATGG AACTAGAGTG GAGTGGAAAG CTGAGAAGTT CGACTGGAAC

Apl_p44-1    ACACCAGATC CGAGGATTAA GTTTAAAAAC AATCCTATCG TAGCGTTGGA
Apl_p44-2    ACACCAGATC CGAGGATTAA GTTTAAAAAC AATCCTATCG TAGCGTTAGA

Apl_p44-3    ACACCAGATC CGAGGATTAA GTTTAAAAAC AATCCTATCG TAGCGTTGGA

Apl_p44-1    AGGAAGTGTG GGCTACAGTA TCGGGGTAGC GAGAGTAGAA CTGGAGATCG
Apl_p44-2    AGGAAGTGTG GGCTACAGTA TCGGGGTAGC GAGAGTAGAA CTGGAGATCG
Apl_p44-3    AGGAAGTGTG GGCTACAGTA TCGGGGTAGC GAGAGTAGAA CTGGAGATCG

Apl_p44-1    GCTATGAACA GTTCAAGACG AAAGGAATAA GAGATACGGG AAGTAAGGAA
Apl_p44-2    GCTATGAACA GTTCAAGACG AAAGGAATAA GAGATACGGG AAGTAAGGAA
Apl_p44-3    GCTATGAACA GTTCAAGACG AAAGGAATAA GAGATACGGG AAGTAAGGAA

Apl_p44-1    GAAGAAGCTG ATGCCGTGTA CCTGTTGGCT AAGAAGCTAC CGCATACCCT
Apl_p44-2    GAAGAAGCTG ATGCCGTGTA CCTGTTGGCT AAGAAGCTAC CGCATACCCT
Apl_p44-3    GAAGAAGCTG ATGCCGTGTA CCTGTTGGCT AAGAAGCTAC CGCATACCCT

Apl_p44-1    GGTGAGTGAC CAGAGCGATA AATTCCTGGA GGAGCTGAAG AATACGAAAG
Apl_p44-2    GGTGAGTGAC CAGAGCGATA AATTCCTGGA GGAGCTGAAG AATACGAAAG
Apl_p44-3    GGTGAGTGAC CAGAGCGATA AATTCCTGGA GGAGCTGAAG AATACGAAAG

Apl_p44-1    CGGCGGAGAT CGTTAAATTT GCTGAGGCTG TTGGCACATC GGCAAAGGAT
Apl_p44-2    CGGCGGAGAT CGTTAAGTTT GCTGAGGCTG TTGGCACATC GGCAAAGGAT
Apl_p44-3    CGGCGGAGAT CGTTAAATTT GCTGAGGCTG TTGGCACATC GGCAAAGGAT

Apl_p44-1    ATTGATAAGA AGGTTTGTAA GAAGCACACT AACAATGCGG CGAACAGTTG
Apl_p44-2    ATTGATGGAA AGGTTTGTAA GAAGCACAAC GGCAATGCGG CAGGCAGTTG
Apl_p44-3    ATTGATGGAA AGGTTTGTAA GAAGAACACT AACAATGCGG CAGACAGTTG
```

Figure 1A continued

```
Apl_p44-1    GAAGTGCGAG CAGCCTGGAA GCGGCACCGA GACAAGCGCC AAGGCGTTCA
Apl_p44-2    GCAGTGCACG CAGACTGGCA GCGAAACAAG CG...GC... AAGACGTTGA
Apl_p44-3    GAAGTGCGAG CAGACTGGCA GCGGCAGCGA CG...GC... AAGGAGTTCA

Apl_p44-1    GTGAAATATT TACGAAGGCA GGCGTAAATA CTGACGGCAA AGGCAAAGCA
Apl_p44-2    GTGAGATATT TACGAAGGCT GGCGTGGATG CTAAC..... .GGCAAAGCA
Apl_p44-3    GTAAACTATT TACGAAGGCT GGCGTGGATG CTAACGAGAA AGGCAAAGCG

Apl_p44-1    TGGCCTAACG GGCACACCGA CAGCGCCGCG AAAGCGGAAG ACCTAAGTAC
Apl_p44-2    TGGCCTAACG GA......AG CGACGCCGCG AAAGCGGAAG ACCTAAGTAC
Apl_p44-3    TGGCCTAACG GGCACACCGA CAGCGCCGCG AAAGCGGAAG ACCTAAGTAC

Apl_p44-1    GGCGTTGAAT AGAGAACTAA CCAGCGCCGA AAAGAACAAG GTAGCTGGGC
Apl_p44-2    TGCGTTGAAT AGAGAACTAA CCAGCGCTGA AAAGAACAAG GTAGCTGGCC
Apl_p44-3    GGCGTTGAAT AGAGAACTAA CCAGCGCCGA AAAGAACAAG GTAGCTGGGC

Apl_p44-1    TGCTAACCAG GACTATATCC GGTGGTGAGG TAGTGGAGAT CCGTGCGGTG
Apl_p44-2    TACTAACCAG GACTATATCC GGTGGCGAGG TAGTGGAGAT CCGTGCGGTG
Apl_p44-3    TGCTAACCAG GACTATATCC GGTGGTGAGG TAGTGGAGAT CCGTGCGGTG

Apl_p44-1    TCGACAACGT CAGTAATGWT AAATGCGTGY TACGATCTGC TGAGC SEQ ID NO:16
Apl_p44-2    TCGACAACGT CAGTAATGAT AAACGCATGT TACGATCTGC TGAGC SEQ ID NO:17
Apl_p44-3    TCGACAACGT CAGTAATGTT AAACGCCTGC TACGATCTGC TGAGC SEQ ID NO:18
```

Figure 1B
Translated Sequence:

```
         ------------------+------------------+------------------+
                          10                 20                 30
         ------------------+------------------+------------------+
  1   Y F Y V G L D Y X P A F S K I N G F E I R E S T G E T A A V   Apl p44-1
  1   Y F Y V G L D Y C P A F S K I N G F E I R E S T G E T A A V   Apl p44-2
  1   Y F Y V G L D Y S P A F S K I N G F E I R E S T G E T A A V   Apl p44-3
  1   Y F Y V G L D Y S P A F S K I R D F S I R E S N G E T K A V   Aph p44-1
         ------------------+------------------+------------------+
                          40                 50                 60
         ------------------+------------------+------------------+
 31   Y P Y M K D G T R V E W K A E K F D W N T P D P R I K F K N   Apl p44-1
 31   Y P Y M K D G T R V E W K A E K F D W N T P D P R I K F K N   Apl p44-2
 31   Y P Y M K D G T R V E W K A E K F D W N T P D P R I K F K N   Apl p44-3
 31   Y P Y L K D G K S V K L E S H K F D W N T P D P R I G F K D   Aph p44-1
         ------------------+------------------+------------------+
                          70                 80                 90
         ------------------+------------------+------------------+
 61   N P I V A L E G S V G Y S I G V A R V E L E I G Y E Q F K T   Apl p44-1
 61   N P I V A L E G S V G Y S I G V A R V E L E I G Y E Q F K T   Apl p44-2
 61   N P I V A L E G S V G Y S I G V A R V E L E I G Y E Q F K T   Apl p44-3
 61   N M L V A M E G S V G Y G I G G A R V E L E I G Y E R F K T   Aph p44-1
         ------------------+------------------+------------------+
                         100                110                120
         ------------------+------------------+------------------+
 91   K G I R D T G S K E E E A D A V Y L L A K K L P H T L V S D   Apl p44-1
 91   K G I R D T G S K E E E A D A V Y L L A K K L P H T L V S D   Apl p44-2
 91   K G I R D T G S K E E E A D A V Y L L A K K L P H T L V S D   Apl p44-3
 91   K G I R D S G S K E D E A D T V Y L L A K E L A Y D V V T G   Aph p44-1
         ------------------+------------------+------------------+
                         130                140                150
         ------------------+------------------+------------------+
121   Q S D K F L E E L K N T K A A E I V K F A E A V G T S A K D   Apl p44-1
121   Q S D K F L E E L K N T K A A E I V K F A E A V G T S A K D   Apl p44-2
121   Q S D K F L E E L K N T K A A E I V K F A E A V G T S A K D   Apl p44-3
121   Q T D N L A A A L A K T S G K D I V Q F A K A V E I S Y P S   Aph p44-1
         ------------------+------------------+------------------+
                         160                170                180
         ------------------+------------------+------------------+
151   I D K K V C K - K H T N N A A N S - - - - - W K C E Q P G S   Apl p44-1
151   I D G K V C K - K H N G N A A G S - - - - - W Q C T Q T G S   Apl p44-2
151   I D G K V C K - K N T N N A A D S - - - - - W K C E Q T G S   Apl p44-3
151   I D G K V C S G K H A A L A A N T N A E K K Y A V E P A N G   Aph p44-1
         ------------------+------------------+------------------+
                         190                200                210
         ------------------+------------------+------------------+
175   G T E T S A K A F S E I F T K A G V N T D G - - - - - - - -   Apl p44-1
175   E T S - - G K T L S E I F T K A G V D A N - - - - - - - - -   Apl p44-2
175   G S D - - G K E F S K L F T K A G V D A N E - - - - - - - -   Apl p44-3
181   G T D G S T S Q C S G L S N G S A E A A H K Y L S K F V S L   Aph p44-1
         ------------------+------------------+------------------+
                         220                230                240
         ------------------+------------------+------------------+
197   - - - - K G K A W P N G H T D - - - - - - - - - - S A A K A   Apl p44-1

194   - - - - - G K A W P N G S - - - - - - - - - - - D A A K A     Apl p44-2
195   - - - - K G K A W P N G H T D - - - - - - - - - - S A A K A   Apl p44-3
211   T G V V E G K N W P T G R S S N N S N S I V V G A P N S N A   Aph p44-1
         ------------------+------------------+------------------+
                         250                260                270
```

Figure 1B Continued

```
        ------------------+------------------+------------------+
213     E D L S T A L N R E L T S A E K N K V A G L L T R T I S G G    Apl p44-1
207     E D L S T A L N R E L T S A E K N K V A G L L T R T I S G G    Apl p44-2
211     E D L S T A L N R E L T S A E K N K V A G L L T R T I S G G    Apl p44-3
241     N A M A K D L V K E L T P E E K T I V A G L L A K T I E G G    Aph p44-1
        ------------------+------------------+------
                        280                290
        ------------------+------------------+------
243     E V V E I R A V S T T S V M X N A C Y D L L S        Apl p44-1  SEQ ID NO:3
237     E V V E I R A V S T T S V M I N A C Y D L L S        Apl p44-2  SEQ ID NO:4
241     E V V E I R A V S T T S V M L N A C Y D L L S        Apl p44-3  SEQ ID NO:5
271     E V V E I R A V S S T S V M V N A C Y D L L S        Aph p44-1  SEQ ID NO:19
```

Figure 2A. Analytical sensitivity of an *Apl* p44 real-time PCR

| Plasmid Concentration | Crossing Point | Melting Temperature (°C) |
|---|---|---|
| 100pg | 17.05 | 66.42 |
| 10pg | 21.04 | 66.44 |
| 1pg | 24.78 | 66.35 |
| 100fg | 28.56 | 66.33 |
| 10fg | 32.57 | 66.73 |
| 1fg | 34.14 | 67.13 |
| 0.1fg | 35.27 | 67.48 |
| Water | Neg | Neg |
| 10fg in canine genomic DNA | 30.02 | 66.66 |
| 0.1fg in canine genomic DNA | 33.25 | 66.43 |

Figure 2B. PCR results of samples and control plasmid tested on the *Aph* and *Apl* p44 real-time PCR

| Sample | *Aph* PCR | | *Apl* PCR | |
|---|---|---|---|---|
| | Crossing Point | Melting Temp | Crossing Point | Melting Temp |
| Turks & Caicos | n/a | n/a | 30.53 | 66.68 |
| Arizona | n/a | n/a | 32.01 | 66.33 |
| Brazil-1 | Negative | Negative | 29.76 | 66.5 |
| Brazil-2 | Negative | Negative | 29.43 | 66.8 |
| Tick-1 | Negative | Negative | 35.84 | 66.88 |
| Tick-2 | Negative | Negative | 30.66 | 66.48 |
| Nymph-1 | Negative | Negative | 30.69 | 66.17 |
| Nymph-2 | Negative | Negative | 33.5 | 66.54 |
| Minnesota | 34.98 | 64.54 | Negative | Negative |
| Massachusetts | 30.89 | 64.58 | Negative | Negative |
| Aph plasmid (1fg) | 36.44 | 64.56 | Negative | Negative |

Figure 3. Comparison of the Snap®4Dx™ *Aph* in-clinic ELISA with *Apl* p44 peptide anti-species, indirect ELISA

| Sample | SNAP® AP result | SNAP® NET AP | Apl p44 | | Sample | SNAP® AP result | SNAP® NET AP | Apl p44 |
|---|---|---|---|---|---|---|---|---|
| P1 | - | 0 | 0.149 | | HP 116 | - | 0.00 | 0.368 |
| P4 | - | 0 | 0.383 | | HP 117 | - | 0.00 | 0.3705 |
| P5 | + | 0.3 | 2.718 | | HP 119 | - | 0.00 | 0.236 |
| P6 | + | 0.22 | 1.773 | | HP 120 | - | 0.00 | 0.220 |
| P7 | - | 0 | 0.2715 | | HP 121 | - | 0.00 | 0.441 |
| P8 | - | 0 | 0.4275 | | HP 123 | + | 0.84 | 2.309 |
| P9 | - | 0 | 0.9595 | | HP 124 | - | 0.00 | 0.316 |
| P12 | - | 0 | 0.6725 | | HP 126 | - | 0.00 | 0.173 |
| P13 | - | 0 | 0.6115 | | HP 127 | - | 0.00 | 0.524 |
| P15 | + | 0.32 | 3.0265 | | HP 128 | - | 0.00 | 0.7555 |
| P16 | - | 0 | 0.222 | | HP 136 | + | 0.75 | 2.509 |
| P18 | - | 0 | 0.4395 | | HP 138 | - | 0.00 | 0.4125 |
| P19 | - | 0 | 0.9025 | | HP 139 | - | 0.00 | 0.204 |
| P20 | - | 0 | 1.492 | | HP 140 | - | 0.00 | 0.5165 |
| P21 | + | 0.07 | 0.5095 | | HP 142 | - | 0.00 | 0.25 |
| P22 | + | 0.18 | 1.716 | | HP 143 | - | 0.00 | 0.348 |
| P23 | + | 0.56 | 2.7275 | | HP 144 | - | 0.00 | 0.246 |
| P25 | - | 0 | 0.114 | | HP 145 | - | 0.00 | 1.057 |
| P26 | + | 0.1 | 0.74 | | HP 146 | - | 0.00 | 0.316 |
| P27 | - | 0 | 0.217 | | HP 148 | - | 0.00 | 0.467 |
| P29 | - | 0 | 0.489 | | HP 149 | - | 0.00 | 0.656 |
| P32 | - | 0 | 0.294 | | HP 150 | - | 0.00 | 0.483 |
| P33 | + | 0.33 | 2.658 | | HP 152 | - | 0.00 | 0.167 |
| P34 | - | 0 | 2.2985 | | HP 153 | - | 0.00 | 0.721 |
| P35 | - | 0 | 0.264 | | HP 154 | - | 0.00 | 0.16 |
| P39 | - | 0 | 0.2535 | | HP 155 | - | 0.00 | 0.1685 |
| P40 | + | 0.15 | 1.346 | | HP 156 | - | 0.00 | 0.209 |
| P41 | - | 0 | 0.678 | | HP 158 | - | 0.00 | 0.32 |
| P43 | - | 0 | 0.841 | | HP 159 | - | 0.00 | 0.2745 |
| P45 | - | 0 | 0.236 | | HP 160 | - | 0.00 | 0.5665 |
| P48 | - | 0 | 1.118 | | HP 170 | + | 0.64 | 2.747 |
| P49 | - | 0 | 0.5345 | | HP 230 | + | 0.58 | 2.747 |
| | | | | | HP 235 | + | 0.48 | 1.563 |
| | | | | | HP 242 | + | 0.75 | 2.131 |
| | | | | | HP 249 | + | 0.55 | 1.376 |

DETECTION OF *ANAPLASMA PLATYS*

BACKGROUND OF THE INVENTION

*Anaplasma platys* (Apl) is an obligate intracellular bacteria that infects platelets and causes a cyclic thrombocytopenia in the dog. The dog appears, at this time, to be the only species affected by this rickettsial agent, and the disease is most likely transmitted by the *Rhipicephalus* spp of ticks. Apl was first reported in the United States in 1978 and has since been reported in Europe, Asia, South America, the Middle East, Australia, and Africa. Because of the common vector, Apl infection is often found as a co-infection with *Ehrlichia canis*. The ability of the organism to produce clinical disease in the dog appears to vary with geography, suggesting that strain differences may contribute to virulence. Apl is related to another *Anaplasma* species known to cause clinical disease in the dog, *Anaplasma phagocytophilum* (Aph). Aph is capable of infecting a wide range of mammals, including humans, and can produce significant morbidity. Clinical signs are usually non-specific and include anorexia, lethargy, lameness, fever, and thrombocytopenia. Aph is transmitted by the *Ixodes* spp of ticks and infections have been reported throughout the United States, the UK, and Europe.

Current diagnostic tests that attempt to distinguish Aph and Apl have limited specificity. PCR for Aph and Apl using 16SrRNA has also had problems with specificity. Therefore, PCR assays for specific detection of Apl are needed in the art. Additionally, serological tests for Apl that use Aph polypeptides or antibodies specific for Apl tend not to detect all instances of Apl infection or exposure. Therefore, serological tests that more accurately detect Apl are needed in the art.

SUMMARY OF THE INVENTION

One embodiment of the invention provides a purified polypeptide comprising SEQ ID NO:12 or at least about 10 contiguous amino acids of SEQ ID NO:12, wherein the at least about 10 contiguous amino acids are chosen from amino acids 16-150 or 209-240 of SEQ ID NO:12. A polypeptide can comprise SEQ ID NO:10; SEQ ID NO:11; SEQ ID NO:13, SEQ ID NO:14 or SEQ ID NO:15. The invention also provides isolated polynucleotides that encode these polypeptides. A purified polypeptide can further comprising a carrier. A purified polypeptide can be in a multimeric form. A purified polypeptide can be linked to an indicator reagent, an amino acid spacer, an amino acid linker, a signal sequence, a stop transfer sequence, a transmembrane domain, a protein purification ligand, a heterologous polypeptide or a combination thereof.

Another embodiment of the invention provides a method of detecting antibodies that specifically bind an *Anaplasma platys* or an *Anaplasma phagocytophilum* polypeptide or both. The method comprises contacting a purified polypeptide of the invention with a test sample, under conditions that allow polypeptide/antibody complexes to form and detecting polypeptide/antibody complexes. The detection of polypeptide/antibody complexes is an indication that antibodies specific for *Anaplasma platys* and/or *Anaplasma phagocytophilum* are present in the test sample, and the absence of polypeptide/antibody complexes is an indication that antibodies specific for *Anaplasma platys* and/or *Anaplasma phagocytophilum* are not present in the test sample. The complexes can be contacted with an indicator reagent prior to the detection step. The amount of antibody in the test sample can be determined. The purified polypeptide can be attached to a substrate. The purified polypeptide can be a fusion protein wherein the purified polypeptide is fused to an indicator reagent, an amino acid spacer, an amino acid linker, a signal sequence, a stop transfer sequence, a transmembrane domain, a protein purification ligand, a heterologous protein, or a combination thereof. The purified polypeptide can be in multimeric form. The method can comprise a microtiter plate assay, reversible flow chromatographic binding assay, an enzyme linked immunosorbent assay, a radioimmunoassay, a hemagglutination assay a western blot assay, a fluorescence polarization immunoassay, or an indirect immunofluorescence assay.

Yet another embodiment of the invention provides a method of detecting an *Anaplasma platys* and/or *Anaplasma phagocytophilum* infection and/or exposure to *Anaplasma platys* and/or *Anaplasma phagocytophilum* in a subject. The method comprises obtaining a biological sample from the subject; contacting a purified polypeptide of the invention with the biological sample under conditions that allow polypeptide/antibody complexes to form; and detecting polypeptide/antibody complexes. The detection of polypeptide/antibody complexes is an indication that the subject has an *Anaplasma platys* and/or *Anaplasma phagocytophilum* infection and/or exposure to *Anaplasma platys* and/or *Anaplasma phagocytophilum*. The absence of polypeptide/antibody complexes is an indication that the mammal has not had an *Anaplasma platys* and/or *Anaplasma phagocytophilum* infection and/or exposure to *Anaplasma platys* and/or *Anaplasma phagocytophilum*. The polypeptide/antibody complexes can be contacted with an indicator reagent that generates a measurable signal prior to the performance of the detection step. The purified polypeptide can be a fusion protein wherein the purified polypeptide is fused to an indicator reagent, an amino acid spacer, an amino acid linker, a signal sequence, a stop transfer sequence, a transmembrane domain, a protein purification ligand, a heterologous protein or a combination thereof. The polypeptide/antibody complexes can detected at about 10 days after exposure or infection of subject by *Anaplasma platys* and/or *Anaplasma phagocytophilum*.

Still another embodiment of the invention provides an antibody that specifically binds to an *Anaplasma platys* p44 polypeptide, wherein the polypeptide comprises at least about 10 contiguous amino acids of SEQ ID NO:12, wherein the at least about 10 contiguous amino acids are chosen from amino acids 16-150 or 209-240 of SEQ ID NO:12. The antibody can be a monoclonal antibody, polyclonal antibody, a Fab fragment, a Fab' fragment, Fab'-SH fragment, F(ab')$_2$ fragment, Fv fragment, or a single chain antibody.

Even another embodiment of the invention provides a method of detecting an *Anaplasma platys* or *Anaplasma phagocytophilum* polypeptide in a sample. The method comprises contacting one or more antibodies that specifically bind to a *Anaplasma platys* polypeptide with the sample under conditions that allow polypeptide/antibody complexes to form; wherein the *Anaplasma platys* polypeptide comprises at least about 10 contiguous amino acids of SEQ ID NO:12, wherein the at least about 10 contiguous amino acids are chosen from amino acids 16-150 or 209-240 of SEQ ID NO:12 and detecting polypeptide/antibody complexes. The detection of polypeptide/antibody complexes is an indication that a *Anaplasma platys* polypeptide is present in the sample and the absence of polypeptide/antibody complexes is an indication that a *Anaplasma platys* polypeptide is not present in the sample.

Another embodiment of the invention provides a method of detecting *Anaplasma platys* p44 polynucleotides. The method comprises contacting a test sample with probe polynucleotides comprising SEQ ID NOs: 6, 7, 8, 9, or combinations thereof, under conditions that allow hybridization complexes between *Anaplasma platys* p44 polynucleotides and the probe polynucleotides; and detecting *Anaplasma platys* p44 polynucleotide/probe polynucleotide complexes; wherein the absence of *Anaplasma platys* p44 polynucleotide/probe polynucleotide complexes is an indication that *Anaplasma platys* polynucleotides are not present in the test sample and wherein the presence of *Anaplasma platys* p44 polynucleotide/probe polynucleotide complexes is an indication that *Anaplasma platys* polynucleotides are present in the test sample.

Yet another embodiment of the invention provides methods of detecting *Anaplasma platys* polynucleotides. The methods comprise contacting a test sample with nucleic acid primers comprising SEQ ID NO:6 and SEQ ID NO:7; and performing a nucleic acid amplification reaction. Amplification products comprising *Anaplasma platys* polynucleotides are produced if *Anaplasma platys* polynucleotides are present in the test sample. Nucleic acid probes comprising SEQ ID NO:8 or SEQ ID NO:9 or both can be used to detect the amplification products. Any *Anaplasma phagocytophilum* polynucleotides present in the test sample may not be amplified. The nucleic acid probes can comprise a detectable label. The nucleic acid amplification reaction can be a polymerase chain reaction (PCR), an end-point PCR, a real-time PCR, a nested PCR assay. The quantity of *Anaplasma platys* polynucleotides in the sample can be determined.

Still another embodiment of the invention provides a method for diagnosing *Anaplasma platys* infection in a subject comprising detecting the presence of polynucleotides that encode all or part of an *Anaplasma platys* p44 polypeptide and/or detecting the presence of an *Anaplasma platys* p44 polypeptide in a test sample.

Even another embodiment of the invention provides a method for detecting and/or quantifying *Anaplasma platys* polynucleotides in a test sample. The method comprises adding sense primers and antisense primers to the test sample under conditions suitable for a polymerase chain reaction, wherein the primers hybridize with *Anaplasma platys* p44 polynucleotides such that an amplification product is formed if *Anaplasma platys* p44 polynucleotides are present in the test sample; and detecting the amplification product, whereby the presence and/or quantity of *Anaplasma platys* p44 polynucleotides are detected. Any *Anaplasma phagocytophilum* polynucleotides present in the test sample may not be amplified.

Therefore, the invention provides methods and compositions for serological detection of *Anaplasma platys* or *Anaplasma phagocytophilum* and nucleic acid-based specific detection of *Anaplasma platys*.

BRIEF DESCRIPTION OF THE DRAWINGS

FIG. 1A shows an alignment of Apl p44 polynucleotide sequences. FIG. 1B shows an alignment of Apl p44 polypeptide sequences.

FIG. 2A shows the analytical sensitivity of a real time PCR assay for Apl p44 polynucleotides. FIG. 2B shows the specificity of a real time PCR assay for Apl p44 polynucleotides.

FIG. 3 shows a comparison of ELISA results using Aph p44 peptide and Apl p44 peptide on a population of serum samples derived from dogs living in areas endemic for *A. platys* and free of *A. phagocytophilum*.

DETAILED DESCRIPTION OF THE INVENTION

The current invention describes polynucleotide sequences for a major outer surface protein of Apl, p44, and peptides from the translated protein that can be used for robust detection of Apl and Aph infection and/or exposure. Additionally, this Apl p44 sequence provides a PCR target to distinguish Apl and Aph infections using, e.g., a real-time PCR with hybridization probes.

Apl Polypeptides

A polypeptide is a polymer of three or more amino acids covalently linked by amide bonds. A polypeptide can be post-translationally modified. A purified polypeptide is a polypeptide preparation that is substantially free of cellular material, other types of polypeptides, chemical precursors, chemicals used in synthesis of the polypeptide, or combinations thereof. A polypeptide preparation that is substantially free of cellular material, culture medium, chemical precursors, chemicals used in synthesis of the polypeptide has less than about 30%, 20%, 10%, 5%, 1% or more of other polypeptides, culture medium, chemical precursors, and/or other chemicals used in synthesis. Therefore, a purified polypeptide is about 70%, 80%, 90%, 95%, 99% or more pure.

One embodiment of the invention provides an Apl p44 polypeptide as shown in SEQ ID NO:12.

```
YFYVGLDYXP AFSKINGFEI RESTGETAAV YPYMKDGTRV

EWKAEKFDWN TPDPRIKFKN NPIVALEGSV GYSIGVARVE

LEIGYEQFKT KGIRDTGSKE EEADAVYLLA KKLPHTLVSD

QSDKFLEELK NTKAAEIVKF AEAVGTSAKD IDXKVCKKXX

XNAAXSWXCX QXGSXXXXXX KXXSXXFTKA GVXXXXXGKA

WPNGXXXXAA KAEDLSTALN RELTSAEKNK VAGLLTRTIS

GGEVVEIRAV STTSVMXNAC YDLLS
```

In one embodiment of the invention the amino acid at position 9 is S or C, the amino acid at position 153 is G or K, the amino acid at position 159 is N or H, the amino acid at position 160 is T or N, the amino acid at position 161 is N or G, the amino acid at position 165 is D, N, or G, the amino acid at position 168 is K or Q, the amino acid at position 170 is E or T, the amino acid at position 172 is T or P, the amino acid at position 175 is G or E, the amino acid at position 176 is S or T, the amino acid at position 177 is D, E, or S, the amino acid at position 178 is T or absent, the amino acid at position 179 is S or absent, the amino acid at position 180 is G or A, the amino acid at position 182 is E, A, or T, the amino acid at position 183 is F or L, the amino acid at position 185 is K or E, the amino acid at position 186 is L or I, the amino acid at position 193 is D or N, the amino acid at position 194 is A or T, the amino acid at position 195 is N or D, the amino acid at position 196 is E, G, or absent, the amino acid at position 197 is K or absent, the amino acid at position 205 is H or S, the amino acid at position 206 is T or absent, the amino acid at position 207 is D or absent, the amino acid at position 208 is S or D, the amino acid at position 257 is L or I. Polypeptides according to SEQ ID NO:12 incorporating any combination of the before mentioned alternative amino acid residues are included in the invention.

One embodiment of the invention is a polypeptide shown in SEQ ID NO:10: KDGTRV EWKAEKFDWNTPDPRI One embodiment of the invention is a polypeptide shown in SEQ ID NO:11: KDGTRV EWKAEKFDWNTPDPRIKFKN One embodiment of the invention is a polypeptide shown in SEQ ID NO:13 RVELEIGYEQFKT KGIRDTGSKEEEADA.

One embodiment of the invention provides a purified polypeptide comprising at least about 20, 25, 30, 40, 50, 60, 70, 80, 90, 100, 110, 120, 130, 140, or more contiguous amino acids, wherein the contiguous amino acids are chosen from amino acids 16-150 or 209-240 of SEQ ID NO:12. The amino acid sequence of Aph p44 has less than 70% identity with Apl p44. Two amino acid sequence regions that are least variable among the different Apl p44 isolates (FIG. 1B), and that are at the same time divergent between p44 from Apl and p44 from Aph, extend from amino acids 16-150 and 209-240 (see, underlining of SEQ ID NO:12, above).

Purified polypeptides of the invention can either be full-length polypeptides or fragments of polypeptides. For example, fragments of polypeptides of the invention can comprise about 10, 15, 20, 50, 75, 100, 150, 200, 250 or more amino acids of polypeptides of the invention. Variant polypeptides are at least about 80, or about 90, 96, 98, or 99% identical to the polypeptide sequences shown in SEQ ID NOs:10, 11, 12, 13, 14, or 15 and are also polypeptides of the invention. Variant polypeptides have one or more conservative amino acid variations or other minor modifications and retain biological activity, i.e., are biologically functional equivalents. A biologically active equivalent has substantially equivalent function when compared to the corresponding wild-type polypeptide.

Percent sequence identity has an art recognized meaning and there are a number of methods to measure identity between two polypeptide or polynucleotide sequences. See, e.g., Lesk, Ed., *Computational Molecular Biology*, Oxford University Press, New York, (1988); Smith, Ed., *Biocomputing: Informatics And Genome Projects*, Academic Press, New York, (1993); Griffin & Griffin, Eds., *Computer Analysis Of Sequence Data, Part I*, Humana Press, New Jersey, (1994); von Heinje, *Sequence Analysis In Molecular Biology*, Academic Press, (1987); and Gribskov & Devereux, Eds., *Sequence Analysis Primer*, M Stockton Press, New York, (1991). Methods for aligning polynucleotides or polypeptides are codified in computer programs, including the GCG program package (Devereux et al., *Nuc. Acids Res.* 12:387 (1984)), BLASTP, BLASTN, FASTA (Atschul et al., *J. Molec. Biol.* 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (*Adv. App. Math.*, 2:482-489 (1981)). For example, the computer program ALIGN which employs the FASTA algorithm can be used, with an affine gap search with a gap open penalty of −12 and a gap extension penalty of −2.

When using any of the sequence alignment programs to determine whether a particular sequence is, for instance, about 95% identical to a reference sequence, the parameters are set such that the percentage of identity is calculated over the full length of the reference polynucleotide and that gaps in identity of up to 5% of the total number of nucleotides in the reference polynucleotide are allowed.

Variants can generally be identified by modifying one of the polypeptide sequences of the invention, and evaluating the properties of the modified polypeptide to determine if it is a biological equivalent. A variant is a biological equivalent if it reacts substantially the same as a polypeptide of the invention in an assay such as an immunohistochemical assay, an enzyme-linked immunosorbent Assay (ELISA), a radioimmunoassay (RIA), immunoenzyme assay or a western blot assay, e.g. has 90-110% of the activity of the original polypeptide. In one embodiment, the assay is a competition assay wherein the biologically equivalent polypeptide is capable of reducing binding of the polypeptide of the invention to a corresponding reactive antigen or antibody by about 80, 95, 99, or 100%. An antibody that specifically binds a corresponding wild-type polypeptide also specifically binds the variant polypeptide. Variant polypeptides of the invention can comprise about 1, 2, 3, 4, 5, 10, or 20 conservative amino acid substitutions.

A conservative substitution is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A polypeptide of the invention can further comprise a signal (or leader) sequence that co-translationally or post-translationally directs transfer of the protein. The polypeptide can also comprise a linker or other sequence for ease of synthesis, purification or identification of the polypeptide (e.g., poly-His), or to enhance binding of the polypeptide to a solid support. For example, a polypeptide can be conjugated to an immunoglobulin Fc region or bovine serum albumin.

A polypeptide can be covalently or non-covalently linked to an amino acid sequence to which the polypeptide is not normally associated with in nature, i.e., a heterologous amino acid sequence. A heterologous amino acid sequence can be from a non-Apl organism (e.g., an Aph organism), a synthetic sequence, or an Apl sequence not usually located at the carboxy or amino terminus of a polypeptide of the invention. Additionally, a polypeptide can be covalently or non-covalently linked to compounds or molecules other than amino acids. For example, a polypeptide can be linked to an indicator reagent, an amino acid spacer, an amino acid linker, a signal sequence, a stop transfer sequence, a transmembrane domain, a protein purification ligand, or a combination thereof. In one embodiment of the invention a protein purification ligand can be one or more C amino acid residues at, for example, the amino terminus or carboxy terminus of a polypeptide of the invention. An amino acid spacer is a sequence of amino acids that are not usually associated with a polypeptide of the invention in nature. An amino acid spacer can comprise about 1, 5, 10, 20, 100, or 1,000 amino acids.

If desired, a polypeptide can be a fusion protein, which can also contain other amino acid sequences, such as amino acid linkers, amino acid spacers, signal sequences, TMR stop transfer sequences, transmembrane domains, as well as ligands useful in protein purification, such as glutathione-S-transferase, histidine tag, and Staphylococcal protein A, or combinations thereof. More than one polypeptide of the invention can be present in a fusion protein. Fragments of polypeptides of the invention can be present in a fusion protein of the invention. A fusion protein of the invention can comprise one or more of Apl polypeptides of the invention, fragments thereof, or combinations thereof.

Polypeptides of the invention can be in a multimeric form. That is, a polypeptide can comprise one or more copies of an Apl polypeptide of the invention or a combination thereof. A multimeric polypeptide can be a multiple antigen peptide (MAP). See e.g., Tam, J. Immunol. Methods, 196:17-32 (1996).

Polypeptides of the invention can comprise an antigen that is recognized by an antibody specific for Apl p44. The antigen can comprise one or more epitopes (i.e., antigenic determinants). An epitope can be a linear epitope, sequential epitope or a conformational epitope. Epitopes within a polypeptide of the invention can be identified by several methods. See, e.g., U.S. Pat. No. 4,554,101; Jameson & Wolf, CABIOS 4:181-186 (1988). For example, a polypeptide of the invention can be isolated and screened. A series of short peptides, which together span an entire polypeptide sequence, can be prepared by proteolytic cleavage. By starting with, for example, 100-mer polypeptide fragments, each fragment can be tested for the presence of epitopes recognized in an ELISA. For example, in an ELISA assay an Apl polypeptide, such as a 100-mer polypeptide fragment, is attached to a solid support, such as the wells of a plastic multi-well plate. A population of antibodies are labeled, added to the solid support and allowed to bind to the unlabeled antigen, under conditions where non-specific absorption is blocked, and any unbound antibody and other proteins are washed away. Antibody binding is detected by, for example, a reaction that converts a colorless substrate into a colored reaction product. Progressively smaller and overlapping fragments can then be tested from an identified 100-mer to map the epitope of interest.

A polypeptide of the invention can be produced recombinantly. A polynucleotide encoding a polypeptide of the invention can be introduced into a recombinant expression vector, which can be expressed in a suitable expression host cell system using techniques well known in the art. A variety of bacterial, yeast, plant, mammalian, and insect expression systems are available in the art and any such expression system can be used. Optionally, a polynucleotide encoding a polypeptide can be translated in a cell-free translation system. A polypeptide can also be chemically synthesized or obtained from Apl cells.

An immunogenic polypeptide of the invention can comprise an amino acid sequence shown in SEQ ID NOs:10, 11, 12, 13, 14, 15 or fragments thereof. An immunogenic polypeptide can elicit antibodies or other immune responses (e.g., T-cell responses of the immune system) that recognize epitopes of a polypeptide having SEQ ID NO:12. An immunogenic polypeptide of the invention can also be a fragment of a polypeptide that has an amino acid sequence shown in SEQ ID NO:12. An immunogenic polypeptide fragment of the invention can be about 10, 15, 20, 25, 30, 40, 50 or more amino acids in length.

Apl Polynucleotides

Polynucleotides of the invention contain less than an entire microbial genome and can be single- or double-stranded nucleic acids. A polynucleotide can be RNA, DNA, cDNA, genomic DNA, chemically synthesized RNA or DNA or combinations thereof. The polynucleotides can be purified free of other components, such as proteins, lipids and other polynucleotides. For example, the polynucleotide can be 50%, 75%, 90%, 95%, 96%, 97%, 98%, 99%, or 100% purified. The polynucleotides of the invention encode the polypeptides described above. In one embodiment of the invention the polynucleotides encode a polypeptide shown in SEQ ID NO:12 or fragments thereof. Polynucleotides of the invention can comprise other nucleotide sequences, such as sequences coding for linkers, signal sequences, TMR stop transfer sequences, transmembrane domains, or ligands useful in protein purification such as glutathione-S-transferase, histidine tag, and Staphylococcal protein A.

Polynucleotides of the invention can be isolated. An isolated polynucleotide is a naturally-occurring polynucleotide that is not immediately contiguous with one or both of the 5' and 3' flanking genomic sequences that it is naturally associated with. An isolated polynucleotide can be, for example, a recombinant DNA molecule of any length, provided that the nucleic acid sequences naturally found immediately flanking the recombinant DNA molecule in a naturally-occurring genome is removed or absent. Isolated polynucleotides also include non-naturally occurring nucleic acid molecules. A nucleic acid molecule existing among hundreds to millions of other nucleic acid molecules within, for example, cDNA or genomic libraries, or gel slices containing a genomic DNA restriction digest are not to be considered an isolated polynucleotide.

Polynucleotides of the invention can also comprise fragments that encode immunogenic polypeptides. Polynucleotides of the invention can encode full-length polypeptides, polypeptide fragments, and variant or fusion polypeptides.

Degenerate nucleotide sequences encoding polypeptides of the invention, as well as homologous nucleotide sequences that are at least about 80, or about 90, 96, 98, or 99% identical to the polynucleotide sequences of the invention and the complements thereof are also polynucleotides of the invention. Percent sequence identity can be calculated as described in the "Polypeptides" section. Degenerate nucleotide sequences are polynucleotides that encode a polypeptide of the invention or fragments thereof, but differ in nucleic acid sequence from the wild-type polynucleotide sequence, due to the degeneracy of the genetic code. Complementary DNA (cDNA) molecules, species homologs, and variants of Apl polynucleotides that encode biologically functional Apl polypeptides also are Apl polynucleotides.

Polynucleotides of the invention can be isolated from nucleic acid sequences present in, for example, a biological sample, such as blood, serum, saliva, or tissue from an infected individual. Polynucleotides can also be synthesized in the laboratory, for example, using an automatic synthesizer. An amplification method such as PCR can be used to amplify polynucleotides from either genomic DNA or cDNA encoding the polypeptides.

Polynucleotides of the invention can comprise coding sequences for naturally occurring polypeptides or can encode altered sequences that do not occur in nature. If desired, polynucleotides can be cloned into an expression vector comprising expression control elements, including for example, origins of replication, promoters, enhancers, or other regulatory elements that drive expression of the polynucleotides of the invention in host cells. An expression vector can be, for example, a plasmid, such as pBR322, pUC, or ColE1, or an adenovirus vector, such as an adenovirus Type 2 vector or Type 5 vector. Optionally, other vectors can be used, including but not limited to Sindbis virus, simian virus 40, alphavirus vectors, poxvirus vectors, and cytomegalovirus and retroviral vectors, such as murine sarcoma virus, mouse mammary tumor virus, Moloney murine leukemia virus, and Rous sarcoma virus. Minichromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

Methods for preparing polynucleotides operably linked to an expression control sequence and expressing them in a host cell are well-known in the art. See, e.g., U.S. Pat. No. 4,366, 246. A polynucleotide of the invention is operably linked when it is positioned adjacent to or close to one or more expression control elements, which direct transcription and/or translation of the polynucleotide.

Polynucleotides of the invention can be used, for example, as probes or primers, for example, PCR primers, to detect the presence of Apl polynucleotides in a test sample, such as a biological sample. Probes are molecules capable of interacting with a target nucleic acid, typically in a sequence specific manner, for example, through hybridization. Primers are a subset of probes that can support an enzymatic manipulation and that can hybridize with a target nucleic acid such that the enzymatic manipulation occurs. A primer can be made from any combination of nucleotides or nucleotide derivatives or analogs available in the art that do not interfere with the enzymatic manipulation.

The hybridization of nucleic acids is well understood in the art and discussed herein. Typically a probe can be made from any combination of nucleotides or nucleotide derivatives or analogs available in the art. The ability of such probes and primers to specifically hybridize to Apl polynucleotide sequences will enable them to be of use in detecting the presence of complementary sequences in a given test sample. Polynucleotide probes and primers of the invention can hybridize to complementary sequences in a test sample such as a biological sample, including saliva, sputum, blood, plasma, serum, urine, feces, cerebrospinal fluid, amniotic fluid, wound exudate, or tissue. Polynucleotides from the sample can be, for example, subjected to gel electrophoresis or other size separation techniques or can be immobilized without size separation. The polynucleotide probes or primers can be labeled. Suitable labels, and methods for labeling probes and primers are known in the art, and include, for example, radioactive labels incorporated by nick translation or by kinase, biotin labels, fluorescent labels, chemiluminescent labels, bioluminescent labels, metal chelator labels and enzyme labels. The polynucleotides from the sample are contacted with the probes or primers under hybridization conditions of suitable stringencies.

Depending on the application, varying conditions of hybridization can be used to achieve varying degrees of selectivity of the probe or primer towards the target sequence. For applications requiring high selectivity, relatively stringent conditions can be used, such as low salt and/or high temperature conditions, such as provided by a salt concentration of from about 0.02 M to about 0.15 M salt at temperatures of from about 50° C. to about 70° C. For applications requiring less selectivity, less stringent hybridization conditions can be used. For example, salt conditions from about 0.14 M to about 0.9M salt, at temperatures ranging from about 20° C. to about 55° C. The presence of a hybridized complex comprising the probe or primer and a complementary polynucleotide from the test sample indicates the presence of Apl or an Apl polynucleotide sequence in the sample.

Antibodies

Antibodies of the invention are antibody molecules that specifically and stably bind to an Apl p44 polypeptide of the invention or fragment thereof. Antibodies of the invention may also specifically and stably bind to an Aph p44 polypeptide or fragment thereof. One of skill in the art can easily determine if an antibody is specific for an Aph or Apl polypeptide using assays described herein. An antibody of the invention can be a polyclonal antibody, a monoclonal antibody, a single chain antibody (scFv), or an antigen binding fragment of an antibody. Antigen-binding fragments of antibodies are a portion of an intact antibody comprising the antigen binding site or variable region of an intact antibody, wherein the portion is free of the constant heavy chain domains of the Fc region of the intact antibody. Examples of antibody fragments include Fab, Fab', Fab'-SH, F(ab')$_2$ and F$_v$ fragments.

An antibody of the invention can be any antibody class, including for example, IgG, IgM, IgA, IgD and IgE. An antibody or fragment thereof binds to an epitope of a polypeptide of the invention. An antibody can be made in vivo in suitable laboratory animals or in vitro using recombinant DNA techniques. Means for preparing and characterizing antibodies are well know in the art. See, e.g., Dean, *Methods Mol. Biol.* 80:23-37 (1998); Dean, *Methods Mol. Biol.* 32:361-79 (1994); Baileg, *Methods Mol. Biol.* 32:381-88 (1994); Gullick, *Methods Mol. Biol.* 32:389-99 (1994); Drenckhahn et al. *Methods Cell. Biol.* 37:7-56 (1993); Morrison, *Ann. Rev. Immunol.* 10:239-65 (1992); Wright et al. *Crit. Rev. Immunol.* 12:125-68 (1992). For example, polyclonal antibodies can be produced by administering a polypeptide of the invention to an animal, such as a human or other primate, mouse, rat, rabbit, guinea pig, goat, pig, dog, cow, sheep, donkey, or horse. Serum from the immunized animal is collected and the antibodies are purified from the plasma by, for example, precipitation with ammonium sulfate, followed by chromatography, such as affinity chromatography. Techniques for producing and processing polyclonal antibodies are known in the art.

"Specifically binds" or "specific for" means that a first antigen, e.g., an Apl or Aph polypeptide, recognizes and binds to an antibody of the invention with greater affinity than other, non-specific molecules. A non-specific molecule is an antigen that shares no common epitope with the first antigen. In this case, Apl or Aph p44 polypeptides would not generally be desirable choices for non-specific control molecules. For example, an antibody raised against a first antigen (e.g., a polypeptide) to which it binds more efficiently than to a non-specific antigen can be described as specifically binding to the first antigen. In a preferred embodiment, an antibody or antigen-binding portion thereof specifically binds to a polypeptide of SEQ ID NO:12 or fragments thereof when it binds with a binding affinity K$_a$ of $10^7$ l/mol or more. Specific binding can be tested using, for example, an enzyme-linked immunosorbant assay (ELISA), a radioimmunoassay (RIA), or a western blot assay using methodology well known in the art.

Additionally, monoclonal antibodies directed against epitopes present on a polypeptide of the invention can also be readily produced. For example, normal B cells from a mammal, such as a mouse, which was immunized with a polypeptide of the invention can be fused with, for example, HAT-sensitive mouse myeloma cells to produce hybridomas. Hybridomas producing Apl- or Aph-specific antibodies can be identified using RIA or ELISA and isolated by cloning in semi-solid agar or by limiting dilution. Clones producing Apl- or Aph-specific antibodies are isolated by another round of screening. Monoclonal antibodies can be screened for specificity using standard techniques, for example, by binding a polypeptide of the invention to a microtiter plate and measuring binding of the monoclonal antibody by an ELISA assay. Techniques for producing and processing monoclonal antibodies are known in the art. See e.g., Kohler & Milstein, Nature, 256:495 (1975). Particular isotypes of a monoclonal antibody can be prepared directly, by selecting from the initial fusion, or prepared secondarily, from a parental hybridoma secreting a monoclonal antibody of a different isotype by using a sib selection technique to isolate class-switch variants. See Steplewski et al., *P.N.A.S. U.S.A.* 82:8653 1985; Spria et al., *J. Immunolog. Meth.* 74:307, 1984. Monoclonal antibodies of the invention can also be recombinant monoclonal antibodies. See, e.g., U.S. Pat. No. 4,474,893; U.S. Pat. No. 4,816,567. Antibodies of the invention can also be chemically constructed. See, e.g., U.S. Pat. No. 4,676,980.

Antibodies of the invention can be chimeric (see, e.g., U.S. Pat. No. 5,482,856), humanized (see, e.g., Jones et al., *Nature* 321:522 (1986); Reichmann et al., Nature 332:323 (1988); Presta, *Curr. Op. Struct. Biol.* 2:593 (1992)), caninized, canine, or human antibodies. Human antibodies can be made by, for example, direct immortilization, phage display, transgenic mice, or a Trimera methodology, see e.g., Reisener et al., *Trends Biotechnol.* 16:242-246 (1998).

Antibodies that specifically bind Apl or Aph antigens (e.g., Apl or Aph polypeptides), are particularly useful for detecting the presence of Apl or Apl antigens in a sample, such as a serum, blood, plasma, urine, fecal, or saliva sample from an Apl- or Aph-infected animal. An immunoassay for Aph or an Apl antigen can utilize one antibody or several antibodies. An immunoassay for Aph or an Apl antigen can use, for example, a monoclonal antibody specific for an Apl epitope, a combination of monoclonal antibodies specific for epitopes of one Apl polypeptide, monoclonal antibodies specific for epitopes of different Apl polypeptides, polyclonal antibodies specific for the same Apl antigen, polyclonal antibodies specific for different Apl antigens, or a combination of monoclonal and polyclonal antibodies. Immunoassay protocols can be based upon, for example, competition, direct reaction, or sandwich type assays using, for example, labeled antibody. Antibodies of the invention can be labeled with any type of label known in the art, including, for example, fluorescent, chemiluminescent, radioactive, enzyme, colloidal metal, radioisotope and bioluminescent labels.

Antibodies of the invention or fragments thereof can be bound to a support and used to detect the presence of Aph or an Apl antigen. Supports include, for example, glass, polystyrene, polypropylene, polyethylene, dextran, nylon, amylases, natural and modified celluloses, polyacrylamides, agaroses and magletite.

Antibodies of the invention can further be used to isolate Apl organisms, Apl antigens, Aph organisms or Aph antigens by immunoaffinity columns. The antibodies can be affixed to a solid support by, for example, adsorption or by covalent linkage so that the antibodies retain their immunoselective activity. Optionally, spacer groups can be included so that the antigen binding site of the antibody remains accessible. The immobilized antibodies can then be used to bind Apl organisms, Apl antigens, Apl organisms, or Apl antigens from a sample, such as a biological sample including saliva, serum, sputum, blood, urine, feces, cerebrospinal fluid, amniotic fluid, wound exudate, or tissue. The bound Apl organisms, Apl antigens, Apl organisms, or Apl antigens are recovered from the column matrix by, for example, a change in pH.

Antibodies of the invention can also be used in immunolocalization studies to analyze the presence and distribution of a polypeptide of the invention during various cellular events or physiological conditions. Antibodies can also be used to identify molecules involved in passive immunization and to identify molecules involved in the biosynthesis of non-protein antigens. Identification of such molecules can be useful in vaccine development. Antibodies of the invention, including, for example, monoclonal antibodies and single chain antibodies, can be used to monitor the course of amelioration of a disease caused by Apl or Aph. By measuring the increase or decrease of Apl antibodies and/or Aph antibodies to Apl antigens and/or Aph antigens in a test sample from an animal, it can be determined whether a particular therapeutic regiment aimed at ameliorating the disorder is effective. Antibodies can be detected and/or quantified using for example, direct binding assays such as RIA, ELISA, or western blot assays.

Methods of Detection

The methods of the invention can be used to detect antibodies or antibody fragments specific for Apl; Apl polypeptides; Aph; Aph polypeptides; Apl polynucleotides, or a combination thereof in a test sample, such as a biological sample, an environmental sample, or a laboratory sample. A test sample can potentially comprise Apl polynucleotides, Apl polypeptides, Aph polypeptides, antibodies specific for Apl, and/or antibodies specific for Aph. A biological sample can include, for example, sera, blood, cells, plasma, or tissue from a mammal such as a horse, cat, dog or human. The test sample can be untreated, precipitated, fractionated, separated, diluted, concentrated, or purified.

In one embodiment methods of the invention comprise contacting an Apl polypeptide with a test sample under conditions that allow a polypeptide/antibody complex, i.e., an immunocomplex, to form. That is, a polypeptide of the invention specifically binds to an antibody specific for Apl and/or Aph antigens located in the sample. One of skill in the art is familiar with assays and conditions that are used to detect antibody/polypeptide complex binding. The formation of a complex between polypeptides and anti-Apl and/or anti-Aph antibodies in the sample is detected. In one embodiment of the invention antibody-polypeptide complexes can be detected at about 10, 15, 20, 25, 30 or less days after exposure or infection of the subject by *Anaplasma platys* and/or *Anaplasma phagocytophilum*.

Antibodies of the invention can be used in a method of the diagnosis of Apl and/or Aph infection by obtaining a test sample from, e.g., a human or animal suspected of having an Apl and/or Aph infection. Exposure to Apl or Aph can also be detected. Exposure would include the presence of Aph or Apl organisms without clinical symptoms and prior infection with Aph or Apl. The test sample is contacted with antibodies of the invention under conditions enabling the formation of antibody-antigen complexes (i.e., immunocomplexes). The amount of antibody-antigen complexes can be determined by methodology known in the art. A level that is higher than that formed in a control sample indicates an Apl and/or Aph infection. A control sample is a sample that does not comprise any Apl and/or Aph polypeptides or antibodies specific for Apl or Aph. In one embodiment of the invention an antibody is specific for Apl antigens only. Alternatively, a polypeptide of the invention can be contacted with a test sample. Apl and/or Aph antibodies in a positive body sample will form an antigen-antibody complex under suitable conditions. The amount of antibody-antigen complexes can be determined by methods known in the art.

In one embodiment of the invention, the polypeptide/antibody complex is detected when an indicator reagent, such as an enzyme conjugate, which is bound to the antibody, catalyzes a detectable reaction. Optionally, an indicator reagent comprising a signal generating compound can be applied to the polypeptide/antibody complex under conditions that allow formation of a polypeptide/antibody/indicator complex. The polypeptide/antibody/indicator complex is detected. Optionally, the polypeptide or antibody can be labeled with an indicator reagent prior to the formation of a polypeptide/antibody complex. The method can optionally comprise a positive or negative control.

In one embodiment of the invention, antibodies of the invention are attached to a solid phase or substrate. A test sample potentially comprising a protein comprising a polypeptide of the invention is added to the substrate. Antibodies that specifically bind polypeptides of the invention are added. The antibodies can be the same antibodies used on the solid phase or can be from a different source or species and can be linked to an indicator reagent, such as an enzyme conjugate. Wash steps can be performed prior to each addition. A chromophore or enzyme substrate is added and color is allowed to develop. The color reaction is stopped and the color can be quantified using, for example, a spectrophotometer.

In another embodiment of the invention, antibodies of the invention are attached to a solid phase or substrate. A test sample potentially comprising a protein comprising a polypeptide of the invention is added to the substrate. Second anti-species antibodies that specifically bind polypeptides of the invention are added. These second antibodies are from a different species than the solid phase antibodies. Third anti-species antibodies are added that specifically bind the second antibodies and that do not specifically bind the solid phase antibodies are added. The third antibodies can comprise and indicator reagent such as an enzyme conjugate. Wash steps can be performed prior to each addition. A chromophore or enzyme substrate is added and color is allowed to develop. The color reaction is stopped and the color can be quantified using, for example, a spectrophotometer.

Assays of the invention include, but are not limited to those based on competition, direct reaction or sandwich-type assays, including, but not limited to enzyme linked immunosorbent assay (ELISA), western blot, IFA, radioimmunoassay (RIA), hemagglutination (HA), fluorescence polarization immunoassay (FPIA), and microtiter plate assays (any assay done in one or more wells of a microtiter plate). One assay of the invention comprises a reversible flow chromatographic binding assay, for example a SNAP® assay. See U.S. Pat. No. 5,726,010.

Assays can use solid phases or substrates or can be performed by immunoprecipitation or any other methods that do not utilize solid phases. Where a solid phase or substrate is used, a polypeptide of the invention is directly or indirectly attached to a solid support or a substrate such as a microtiter well, magnetic bead, non-magnetic bead, column, matrix, membrane, fibrous mat composed of synthetic or natural fibers (e.g., glass or cellulose-based materials or thermoplastic polymers, such as, polyethylene, polypropylene, or polyester), sintered structure composed of particulate materials (e.g., glass or various thermoplastic polymers), or cast membrane film composed of nitrocellulose, nylon, polysulfone or the like (generally synthetic in nature). A preferred substrate is sintered, fine particles of polyethylene, commonly known as porous polyethylene, for example, 10-15 micron porous polyethylene from Chromex Corporation (Albuquerque, N. Mex.). All of these substrate materials can be used in suitable shapes, such as films, sheets, or plates, or they may be coated onto or bonded or laminated to appropriate inert carriers, such as paper, glass, plastic films, or fabrics. Suitable methods for immobilizing peptides on solid phases include ionic, hydrophobic, covalent interactions and the like.

In one type of assay format, one or more polypeptides can be coated on a solid phase or substrate. A test sample suspected of containing an anti-Apl and/or anti-Aph antibody or fragment thereof is incubated with an indicator reagent comprising a signal generating compound conjugated to an antibody or antibody fragment specific for Apl and/or Aph for a time and under conditions sufficient to form antigen/antibody complexes of either antibodies of the test sample to the polypeptides of the solid phase or the indicator reagent compound conjugated to an antibody specific for Apl and/or Aph to the polypeptides of the solid phase. The reduction in binding of the indicator reagent conjugated to an anti-Apl and/or anti-Aph antibody to the solid phase can be quantitatively measured. A measurable reduction in the signal compared to the signal generated from a confirmed negative Apl and/or Aph test sample indicates the presence of anti-Apl and/or anti-Aph antibody in the test sample. This type of assay can quantitate the amount of anti-Apl and/or anti-Aph antibodies in a test sample.

In another type of assay format, one or more polypeptides of the invention are coated onto a support or substrate. A polypeptide of the invention is conjugated to an indicator reagent and added to a test sample. This mixture is applied to the support or substrate. If Apl and/or Aph antibodies are present in the test sample they will bind the polypeptide conjugated to an indicator reagent and to the polypeptide immobilized on the support. The polypeptide/antibody/indicator complex can then be detected. This type of assay can quantitate the amount of anti-Apl and/or anti-Aph antibodies in a test sample.

In another type of assay format, one or more polypeptides of the invention are coated onto a support or substrate. The test sample is applied to the support or substrate and incubated. Unbound components from the sample are washed away by washing the solid support with a wash solution. If Apl specific and/or Aph specific antibodies are present in the test sample, they will bind to the polypeptide coated on the solid phase. This polypeptide/antibody complex can be detected using a second species-specific antibody that is conjugated to an indicator reagent. The polypeptide/antibody/anti-species antibody indicator complex can then be detected. This type of assay can quantitate the amount of anti-Apl and/or anti-Aph antibodies in a test sample.

The formation of a polypeptide/antibody complex or a polypeptide/antibody/indicator complex can be detected by radiometric, colormetric, fluorometric, size-separation, or precipitation methods. Optionally, detection of a polypeptide/antibody complex is by the addition of a secondary antibody that is coupled to an indicator reagent comprising a signal generating compound. Indicator reagents comprising signal generating compounds (labels) associated with a polypeptide/antibody complex can be detected using the methods described above and include chromogenic agents, catalysts such as enzyme conjugates fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors, magnetic particles, and the like. Examples of enzyme conjugates include alkaline phosphatase, horseradish peroxidase, beta-galactosidase, and the like. The selection of a particular label is not critical, but it will be capable of producing a signal either by itself or in conjunction with one or more additional substances.

Formation of the complex is indicative of the presence of anti-Apl and/or anti-Aph antibodies in a test sample. Therefore, the methods of the invention can be used to diagnose Apl and/or Aph infection in a patient.

The methods of the invention can also indicate the amount or quantity of anti-Apl and/or Aph antibodies in a test sample. With many indicator reagents, such as enzyme conjugates, the amount of antibody present is proportional to the signal generated. Depending upon the type of test sample, it can be diluted with a suitable buffer reagent, concentrated, or contacted with a solid phase without any manipulation. For example, it usually is preferred to test serum or plasma samples that previously have been diluted, or concentrate specimens such as urine, in order to determine the presence and/or amount of antibody present.

The invention further comprises assay kits (e.g., articles of manufacture) for detecting anti-Apl and/or anti-Aph antibodies or antibody fragments, Apl, Apl polypeptides, Aph, and/or Aph polypeptides in a sample. A kit comprises one or more polypeptides of the invention and means for determining binding of the polypeptide to anti-Apl antibodies and/or or anti-Aph antibodies or antibody fragments in the sample. A kit or article of manufacture can also comprise one or more antibodies or antibody fragments of the invention and means for determining binding of the antibodies or antibody fragments to Apl, Apl polypeptides, Aph, and/or Aph polypeptides in the sample. A kit can comprise a device containing one or more polypeptides or antibodies of the invention and instructions for use of the one or more polypeptides or antibodies for, e.g., the identification of an Apl and/or Aph infection in a mammal. The kit can also comprise packaging material comprising a label that indicates that the one or more polypeptides or antibodies of the kit can be used for the identification of Apl and/or Aph infection. Other components such as buffers, controls, and the like, known to those of ordinary skill in art, can be included in such test kits. The polypeptides, antibodies, assays, and kits of the invention are useful, for example, in the diagnosis of individual cases of Apl and/or Aph infection in a patient, as well as epidemiological studies of Apl and/or Aph outbreaks. Exposure to Apl or Aph can also be detected. Exposure would include the presence of Aph or Apl organisms without clinical symptoms and prior infection with Aph or Apl.

Polypeptides and assays of the invention can be combined with other polypeptides or assays to detect the presence of Apl along with other organisms. For example, polypeptides and assays of the invention can be combined with reagents that detect heartworm and/or *Borrelia burgdorferi* and/or *Anaplasma phagocytophilium* and/or *Ehrlichia canis*.

Polynucleotides of the invention can be used to detect the presence of Apl polynucleotides in a sample. The polynucleotides can be used to detect Apl polynucleotides in a sample by a simple hybridization reaction and can also be used in, e.g., polymerase chain reactions (PCR) such as a real-time PCR reaction. Methods and compositions of the invention can also be used to differentially detect the presence Apl from Aph.

PCR assays are well described in the art, including, for example, U.S. Pat. No. 4,683,195; U.S. Pat. No. 4,683,202; U.S. Pat. No. 4,965,188. Generally, polynucleotide primers are annealed to denatured strands of a target nucleic acid. Primer extension products are formed by polymerization of deoxynucleoside triphosphates by a polymerase. PCR then involves repetitive cycles of template nucleic acid denaturation, primer annealing and extension of the annealed primers by the action of a thermostable polymerase. The process results in exponential amplification of the target Apl nucleic acids in the test sample, which allows for the detection of target polynucleotides existing in very low concentrations in a sample.

Real-time PCR assays are based on the detection of a signal, e.g., a fluorescent reporter signal. This signal increases in direct proportion to the amount of PCR product in a reaction. Real-time PCR is any amplification technique that makes it possible to monitor the evolution of an ongoing amplification reaction. See, Quantitation of DNA/RNA Using Real-Time PCR Detection, Perkin Elmer Applied Biosystems (1999); PCR Protocols (Academic Press New York, 1989). By recording the amount of fluorescence emission at each cycle, it is possible to monitor the PCR reaction during exponential phase where the first significant increase in the amount of PCR product correlates to the initial amount of target template. The higher the starting copy number of the nucleic acid target, the sooner a significant increase in fluorescence is observed.

One embodiment of the invention provides a method for detecting and/or quantifying *Anaplasma platys* polynucleotides in a test sample. Sense primers and antisense primers can be added to a test sample under conditions suitable for a polymerase chain reaction. The primers hybridize with *Anaplasma platys* p44 polynucleotides such that an amplification product is formed if *Anaplasma platys* p44 polynucleotides are present in the test sample. In one embodiment, the primers are SEQ ID NOs:6 and 7. Amplification products are detected and the presence and/or quantity of *Anaplasma platys* p44 polynucleotides is determined. Amplification products can be detected with a polynucleotide probe that hybridizes, under conditions suitable for a polymerase chain reaction, with an Apl p44 polynucleotide sequence. Examples of probes include SEQ ID NOs:8 and 9. The amplification product can be quantified by measuring a detection signal from the probe and comparing said detection signal to a second probe detection signal from a quantification standard. The quantification standard can be extracted in parallel with the test sample.

In another embodiment of the invention PCR primers can be selected from the variable regions of an Apl p44 polynucleotide. For example, primers of 10, 15, 20, 25, 30, or 40 contiguous nucleotides can be selected from the region between position 20 and 450 of SEQ ID NOs: 16, 17 and/or 18.

All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

EXAMPLES

Example 1

Cloning of a p44 Homolog from Apl

A homolog of an Aph p44 gene from Apl was cloned from the blood of an infected dog. The blood sample was obtained from a dog residing on the Hopi Reservation in Arizona. Genomic DNA was isolated from 200 ul of whole blood using standard techniques (QiaAmp DNA Blood Miniprep Kit—Part #51104). Degenerate primers were designed to target the conserved regions of Aph p44, *Anaplasma marginale* msp2, *Anaplasma ovis* msp2, and *Anaplasma centrale* msp2 genes (Forward primer: 5' TAT TTT TAT GTT GGT YTR GAY TAT WSH CC 3' (SEQ ID NO:1) Reverse primer: 5' GCT CAG CAG ATC GTA RCA NGC RTT YAW CAT 3' (SEQ ID NO:2)).

Degenerate primer-based PCR on a conventional thermocycler was used to amplify a polynucleotide with a length of approximately 800 nucleotides from an Apl p44 gene according to standard protocols (Platinum® Taq, Invitrogen). PCR products were cloned, sequenced, and analyzed relative to those reported for other species of *Anaplasma*. FIG. 1A shows an alignment of the partial sequences obtained from different isolates of Apl p44. The cloned Apl p44 gene contained a hypervariable region flanked by conserved sequences at the 5' and 3' ends. This is similar to Aph p44, but the length of the hypervariable region was shorter for Apl p44. FIG. 1B shows an amino acid alignment for Apl p44 with the corresponding region from a published Aph sequence (Aph p44-1; Accession No. ABA26590). While Apl p44 nucleotide sequences of present the invention (e.g. FIG. 1A) show greater than 90% identity to each other, they share less than 70% identity with that of Aph p44, and the same is true for the amino acid sequences.

Example 2

Detection of Apl by Real Time PCR Assay

A real-time PCR assay was developed to detect an Apl p44 polynucleotide from genomic DNA. Sample types for analysis included canine whole blood, as well as nymph and adult ticks. Primers and hybridization probes were selected to be specific for an Apl p44 gene and did not amplify the p44 gene of Aph. Sequences of the primers and probes are shown below:

```
Apl p44 forward primer:
5' CCGGCGTTTAGTAAGATAAATG 3'         (SEQ ID NO: 6)

Apl p44 reverse primer:
5' GCAAATTTAACGATCTCCGCC 3'          (SEQ ID NO: 7)

Apl p44 probe 1129-FITC:
5' ACAGTATCGGGGTAGCGAGAGTAGAA 3'     (SEQ ID NO: 8)

Apl p44 probe 1183-LC670:
5' GGAGATCGGCTATGAACAGTTCAAGAC 3'    (SEQ ID NO: 9)
```

These were synthesized by a commercial vendor. The real-time PCR was optimized for the Roche LightCycler® 480 using Roche reagents (Genotyping Master Mix #04707524001). Primers were used at a concentration of 0.3 μM for the forward primer and 0.6 μM for the reverse primer. Both probes were used at a concentration of 0.3 μM. PCR was performed under the following conditions: a single hot-start cycle at 95° C. for 10 minutes followed by 50 cycles of denaturation at 95° C. for 30 seconds, annealing at 58° C. for 25 seconds, and extension at 72° C. for 20 seconds. A melting curve was performed by heating the PCR product to 95° C. for 1 minute, cooling to 40° C. for one minute, and then gradually heating to 80° C. Positive samples were identified from the software as having both positive crossing points and a melting curve temperature of 66.5° C.+/−1° C. Analytical sensitivity was determined to be at least 0.1 fg in negative canine genomic DNA (FIG. 2A). The Apl p44 PCR detected strains of Apl from across the US, the Caribbean and Brazil. The Apl p44 PCR did not detect Aph p44 DNA from a control plasmid containing the Aph p44 template or PCR-positive field samples (FIG. 2B).

Example 3

Detection of Apl by an Anti-Species, Indirect ELISA

A synthetic peptide derived from the p44 gene of Apl was tested in an ELISA format to determine serological reactivity in dogs from an area with a high burden of *Rhipicephalus* ticks and high seroprevalence for *E. canis*. These geographic areas have been shown to have relatively high levels of *A. platys* infections and an absence of *A. phagocytophilum* infections in dogs by PCR. The peptide sequence is shown below:

```
                                     (SEQ ID NO: 15)
Cys-Lys-Asp-Gly-Thr-Arg-Val-Glu-Trp-Lys-Ala-Glu-
Lys-Phe-Asp-Trp-Asn-Thr-Pro-Asp-Pro-Arg-Ile.
```

An alternate peptide sequence comprises:

```
                                     (SEQ ID NO: 14)
Cys-Lys-Asp-Gly-Thr-Arg-Val-Glu-Trp-Lys-Ala-Glu-
Lys-Phe-Asp-Trp-Asn-Thr-Pro-Asp-Pro-Arg-Ile-Lys-
Phe-Lys-Asn
```

The synthetic peptide of SEQ ID NO: 15 was solubilized in DMSO and coated on Immulon 2Hb plates (Thermo Electron Corporation #3455) at a concentration of 0.25 μg/ml in 50 mM Tris, pH 7.5 overnight at room temperature. The plates were blocked with a Tris/TWEEN® buffer (0.1M Tris, pH 7.6 with 2% TWEEN® 20) for 4 hours. The plates were washed three times with plate wash (PBS, pH 7.2 with 0.05% TWEEN®20). Serum was added at a 1:100 dilution in sample diluent (PBS, pH 7.2 with 0.05% TWEEN®20 and 1% BSA) and allowed to incubate at room temperature for 1 hour. Plates were washed 5 times and a anti-dog conjugate (Jackson ImmunoResearch # 304-035-003) was added at a 1:2000 dilution in sample diluent and allowed to incubate for 1 hour at room temperature. The plates were washed 3 times and a one component TMB substrate was added and allowed to incubate for 5 minutes before the reaction was stopped with 1% SDS. Absorbance measurements were read on a standard plate reader at a wavelength of 650 nm. A cut-off of 0.4 was determined. Samples were compared to a similar in-clinic ELISA for Aph p44 (Snap®4DX™, IDEXX Laboratories, Inc.) and the results are shown in FIG. 3. The column labeled "SNAP® AP result" shows results obtained by visual inspection. The column labeled "SNAP® NET AP" shows quantitative results obtained by densitometric measurement.

A total of 67 samples were tested. Twenty-seven samples tested negative and 16 samples tested positive on both assays. Twenty-four samples tested negative on the in-clinic ELISA for Aph p44, but tested positive by the Apl p44 anti-species, indirect ELISA. Thus, the Apl assay detects Apl exposure in dogs that would be missed by testing with Aph assays.

Apl p44 provides a means of detecting Apl infection beyond what is identified by cross-reactivity to the p44 from Aph. Apl p44 polynucleotides allow for differentiation between Apl and Aph.

Example 4

Sensitivity of Direct Apl ELISA

Dogs were experimentally infected with Apl and serum samples were collected following a time course. Serum antibodies to Apl were assayed using a direct Apl ELISA and the SNAP® 4Dx. Specifically, the synthetic peptide derived from the p44 gene of Apl (SEQ ID NO:14, and designated as Apl_p44L in Tables 1 and 2) was solubilized in DMSO and coated on Immulon™ 2Hb plates (Thermo Electron Corporation #3455) at a concentration of 0.25 μg/ml in 50 mM Sodium Carbonate, pH 9.6, overnight at room temperature. The plates were blocked (2% TWEEN®20 in 0.1M Tris, pH 7.6) for 2 hours. Serum (25 ul) was mixed with 50 ul of a specific conjugate (the conjugate, Apl_p44L: HRPO, was made at 1:1 ratio and diluted to 0.5 g/ml in 50 mM Tris pH 7.6, 0.05% TWEEN®20, 5% BSA, and 10% FBS), and added immediately to coated well for incubation at room temperature for 1 hour. Plates were then washed 6 times before a one component TMB substrate was added for color development. Absorbance measurements were read on a standard plate reader at a wavelength of 650 nm. A cut-off of 0.07 was determined. The same samples were also tested using an in-clinic ELISA developed for Aph (Snap®4Dx™, IDEXX Laboratories, Inc.) and the results are shown in Table 1 (the column labeled "SNAP® NET AP" shows quantitative results obtained by densitometric measurement. "Days PI" refers to the number of days post-infection.)

TABLE 1

Time course study by Apl p44 peptide ELISA

| Canine ID | IDEXX ID | Apl_P44L cutoff 0.07 | SNAP® NET AP | Days PI |
|---|---|---|---|---|
| 105376 | A1_0 | 0.03 | 0 | 3 |
| | A1_1 | 0.04 | 0 | 7 |
| | A1_2 | 0.45 | 0 | 10 |
| | A1_3 | 0.68 | 0 | 14 |
| | A1_4 | 0.37 | 0.01 | 17 |
| | A1_5 | 0.17 | 0.03 | 21 |
| | A1_6 | 0.07 | 0.05 | 24 |
| | A1_7 | 0.11 | 0.2 | 28 |
| | A1_8 | 0.26 | 0.34 | 35 |
| | A1_9 | 0.20 | 0.31 | 42 |
| | A1_10 | 0.25 | 0.29 | 49 |
| | A1_11 | 0.20 | 0.13 | 56 |
| | A1_12 | 0.46 | 0.18 | 63 |
| | A1_13 | 1.11 | 0.43 | 71 |
| | A1_15 | 0.32 | 0.17 | 84 |
| 125011 | A2_0 | 0.03 | 0 | 3 |
| | A2_1 | 0.03 | 0 | 7 |
| | A2_2 | 0.24 | 0.05 | 10 |
| | A2_3 | 0.20 | 0.15 | 13 |
| | A2_4 | 0.17 | 0.02 | 17 |
| | A2_5 | 0.10 | 0.11 | 21 |
| | A2_6 | 0.07 | 0.15 | 24 |
| | A2_7 | 0.07 | 0.29 | 28 |
| | A2_8 | 0.15 | 0.38 | 35 |
| | A2_9 | 0.21 | 0.41 | 42 |
| | A2_10 | 0.19 | 0.29 | 49 |
| | A2_11 | 0.18 | 0.24 | 56 |
| | A2_12 | 0.14 | 0.2 | 64 |
| | A2_13 | 0.17 | 0.11 | 71 |
| | A2_14 | 0.20 | 0.09 | 78 |
| | A2_15 | 0.19 | 0.11 | 86 |
| 257818 | A3_0 | 0.03 | 0 | 3 |
| | A3_1 | 0.03 | 0 | 7 |
| | A3_2 | 0.21 | 0 | 10 |
| | A3_3 | 0.23 | 0 | 13 |
| | A3_4 | 0.23 | 0.02 | 17 |
| | A3_5 | 0.13 | 0.06 | 21 |
| | A3_6 | 0.11 | 0.01 | 24 |
| | A3_7 | 0.15 | 0.15 | 28 |
| | A3_8 | 0.37 | 0.27 | 35 |
| | A3_9 | 0.49 | 0.24 | 42 |
| | A3_10 | 0.58 | 0.22 | 49 |
| | A3_11 | 0.55 | 0.23 | 56 |
| | A3_12 | 0.54 | 0.16 | 64 |
| | A3_13 | 0.49 | 0.1 | 71 |

TABLE 1-continued

Time course study by Apl p44 peptide ELISA

| Canine ID | IDEXX ID | Apl_P44L cutoff 0.07 | SNAP® NET AP | Days PI |
|---|---|---|---|---|
| | A3_14 | 1.28 | 0.28 | 78 |
| | A3_15 | 1.39 | 0.25 | 86 |
| 264347 | A4_0 | 0.03 | 0 | 3 |
| | A4_1 | 0.03 | 0 | 7 |
| | A4_2 | 0.04 | 0 | 10 |
| | A4_3 | 0.06 | 0 | 14 |
| | A4_4 | 0.08 | 0 | 17 |
| | A4_5 | 0.05 | 0.05 | 21 |
| | A4_6 | 0.04 | 0.09 | 24 |
| | A4_7 | 0.06 | 0.05 | 28 |
| | A4_8 | 0.07 | 0.09 | 35 |
| | A4_9 | 0.07 | 0.08 | 42 |
| | A4_10 | 0.09 | 0.07 | 49 |
| | A4_11 | 0.11 | 0.06 | 56 |
| | A4_12 | 0.20 | 0.04 | 63 |
| | A4_13 | 0.37 | 0.06 | 71 |
| | A4_14 | 1.41 | 0.27 | 79 |
| | A4_15 | 0.24 | 0.06 | 84 |
| 280610 | A5_0 | 0.03 | 0 | 3 |
| | A5_1 | 0.03 | 0 | 7 |
| | A5_2 | 0.06 | 0 | 10 |
| | A5_3 | 0.58 | 0 | 14 |
| | A5_4 | 0.42 | 0 | 17 |
| | A5_5 | 0.12 | 0 | 21 |
| | A5_6 | 0.07 | 0.08 | 24 |
| | A5_7 | 0.14 | 0.16 | 28 |
| | A5_8 | 0.08 | 0.07 | 35 |
| | A5_9 | 0.40 | 0.06 | 42 |
| | A5_10 | 0.53 | 0.04 | 49 |
| | A5_11 | 0.70 | 0.06 | 56 |
| | A5_12 | 0.88 | 0.27 | 63 |
| | A5_13 | 0.78 | 0.06 | 71 |
| | A5_14 | 1.45 | 0.14 | 79 |
| | A5_15 | 0.73 | 0.08 | 84 |
| 287099 | A6_0 | 0.03 | 0 | 3 |
| | A6_1 | 0.03 | 0 | 7 |
| | A6_2 | 0.71 | 0 | 10 |
| | A6_3 | 0.95 | 0.03 | 13 |
| | A6_4 | 0.40 | 0.03 | 17 |
| | A6_5 | 0.13 | 0 | 21 |
| | A6_6 | 0.07 | 0 | 24 |
| | A6_7 | 0.10 | 0.09 | 28 |
| | A6_8 | 0.10 | 0.18 | 34 |
| | A6_9 | 0.15 | 0.16 | 42 |
| | A6_10 | 0.22 | 0.2 | 49 |
| | A6_11 | 0.36 | 0.28 | 56 |
| | A6_12 | 0.26 | 0.11 | 62 |
| | A6_13 | 0.41 | 0.17 | 70 |
| | A6_14 | 1.08 | 0.46 | 78 |
| | A6_15 | 0.90 | 0.36 | 83 |

The results show that a direct ELISA assay using peptide Apl-p44L (SEQ ID NO:14) detected an immune response to Apl in serum of experimentally infected dogs. The results further show that the Apl assay detected an immune response to Apl earlier than the in-clinic Aph ELISA. In four of the six dogs, a response was detected at day 10 post-infection.

Example 5

Detection of Aph Infection by Apl ELISA

The same direct ELISA procedure described in Example 4, based on Apl_p44L peptide (SEQ ID NO:14), was used to test serum samples that were previously tested positive for Aph infection. These include samples from dogs experimentally infected with Aph (i.e. Pinky and Brain), as well as field dogs from an area with a high Aph seroprevalence (with ME as prefix in ID). Five samples from an area with a high Apl seroprevalence (i.e. P or HP as prefix in ID) were used as positive controls, and five from normal dogs (RAR as prefix in ID) served as negative controls. The same set of samples were also tested using an in-clinic ELISA developed for Aph (Snap®4DX™, IDEXX Laboratories, Inc.) and the results are shown in Table 2 (the column labeled "SNAP® NET AP" shows quantitative results obtained by densitometric measurement.)

TABLE 2

Detection of Aph infection by Apl p44 peptide ELISA

| ID | Apl p44L cut off 0.07 | SNAP® (net AP) |
|---|---|---|
| ME307 | 0.11 | 0.55 |
| ME308 | 0.27 | 0.30 |
| ME314 | 0.05 | 0.09 |
| ME478 | 0.05 | 0.12 |
| ME485 | 0.10 | 0.52 |
| ME487 | 0.04 | – |
| ME492 | 0.55 | 0.47 |
| ME513 | 0.09 | 0.04 |
| ME562 | 0.05 | 0.42 |
| ME593 | 0.04 | 0.34 |
| ME631 | 0.10 | 0.27 |

TABLE 2-continued

Detection of Aph infection by Apl p44 peptide ELISA

| ID | Apl p44L cut off 0.07 | SNAP® (net AP) |
|---|---|---|
| ME635 | 0.26 | 0.44 |
| ME668 | 0.06 | 0.66 |
| ME703 | 0.04 | 0.58 |
| ME724 | 0.14 | 0.10 |
| ME741 | 0.08 | 0.05 |
| ME758 | 0.08 | 0.13 |
| pinky 62 | 0.62 | + |
| Brain 69 | 0.21 | + |
| p9 | 0.62 | – |
| p34 | 1.75 | – |
| p43 | 0.22 | – |
| HP127 | 0.12 | – |
| HP145 | 0.20 | – |
| RAR 1758 | 0.03 | – |
| RAR 1769 | 0.04 | – |
| RAR 1755 | 0.03 | – |
| RAR 1756 | 0.03 | – |
| RAR 1760 | 0.03 | – |
| BLK | 0.03 | |

We claim:

1. A purified polypeptide comprising an amino acid sequence set forth as SEQ ID NO:10, SEQ ID NO:11, SEQ ID NO:14, or SEQ ID NO:15.

2. The purified polypeptide of claim 1, further comprising a carrier.

3. The purified polypeptide of claim 1, wherein the purified polypeptide is in a multimeric form.

4. The purified polypeptide of claim 1, wherein the purified polypeptide is linked to an indicator reagent, an amino acid spacer, an amino acid linker, a signal sequence, a stop transfer sequence, a transmembrane domain, a protein purification ligand, a heterologous polypeptide or a combination thereof.

5. A purified polypeptide comprising at least 15 contiguous amino acids of an amino acid sequence set forth as SEQ ID NO:10, SEQ ID NO:11, SEQ ID NO:14, or SEQ ID NO:15.

6. The purified polypeptide of claim 5, further comprising a carrier.

7. The purified polypeptide of claim 5, wherein the purified polypeptide is in a multimeric form.

8. The purified polypeptide of claim 5, wherein the purified polypeptide is linked to an indicator reagent, an amino acid spacer, an amino acid linker, a signal sequence, a stop transfer sequence, a transmembrane domain, a protein purification ligand, a heterologous polypeptide or a combination thereof.

* * * * *

UNITED STATES PATENT AND TRADEMARK OFFICE
CERTIFICATE OF CORRECTION

PATENT NO. : 7,507,789 B2  Page 1 of 1
APPLICATION NO. : 11/697769
DATED : March 24, 2009
INVENTOR(S) : Beall et al.

It is certified that error appears in the above-identified patent and that said Letters Patent is hereby corrected as shown below:

Title Page, Item (75): "Melissa Jane Beall, Yarmouth, ME" should be:
--Melissa Jane Beall, Cape Elizabeth, ME--

Signed and Sealed this

Twenty-fourth Day of November, 2009

David J. Kappos
*Director of the United States Patent and Trademark Office*

SEQUENCE LISTING

```
<160> NUMBER OF SEQ ID NOS: 19

<210> SEQ ID NO 1
<211> LENGTH: 29
<212> TYPE: DNA
<213> ORGANISM: Artificial
<220> FEATURE:
<223> OTHER INFORMATION: Degenerate primer to amplify Anaplasma platys
      p44 polynucleotide

<400> SEQUENCE: 1
tatttttatg ttggtytrga ytatwshcc                                        29

<210> SEQ ID NO 2
<211> LENGTH: 30
<212> TYPE: DNA
<213> ORGANISM: Artificial
<220> FEATURE:
<223> OTHER INFORMATION: Degenerate primer to amplify Anaplasma playts
      polynucleotide
<220> FEATURE:
<221> NAME/KEY: misc_feature
<222> LOCATION: (19)..(19)
<223> OTHER INFORMATION: n is a, c, g, or t

<400> SEQUENCE: 2
gctcagcaga tcgtarcang crttyawcat                                       30

<210> SEQ ID NO 3
<211> LENGTH: 265
<212> TYPE: PRT
<213> ORGANISM: Anaplasma playts
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (257)..(257)
<223> OTHER INFORMATION: Xaa can be any naturally occurring amino acid
```

```
<400> SEQUENCE: 3

Tyr Phe Tyr Val Gly Leu Asp Tyr Xaa Pro Ala Phe Ser Lys Ile Asn
1               5                   10                  15

Gly Phe Glu Ile Arg Glu Ser Thr Gly Glu Thr Ala Ala Val Tyr Pro
            20                  25                  30

Tyr Met Lys Asp Gly Thr Arg Val Glu Trp Lys Ala Glu Lys Phe Asp
        35                  40                  45

Trp Asn Thr Pro Asp Pro Arg Ile Lys Phe Lys Asn Asn Pro Ile Val
    50                  55                  60

Ala Leu Glu Gly Ser Val Gly Tyr Ser Ile Gly Val Ala Arg Val Glu
65                  70                  75                  80

Leu Glu Ile Gly Tyr Glu Gln Phe Lys Thr Lys Gly Ile Arg Asp Thr
                85                  90                  95

Gly Ser Lys Glu Glu Glu Ala Asp Ala Val Tyr Leu Leu Ala Lys Lys
            100                 105                 110

Leu Pro His Thr Leu Val Ser Asp Gln Ser Asp Lys Phe Leu Glu Glu
        115                 120                 125

Leu Lys Asn Thr Lys Ala Ala Glu Ile Val Lys Phe Ala Glu Ala Val
    130                 135                 140

Gly Thr Ser Ala Lys Asp Ile Asp Lys Lys Val Cys Lys Lys His Thr
145                 150                 155                 160

Asn Asn Ala Ala Asn Ser Trp Lys Cys Glu Gln Pro Gly Ser Gly Thr
                165                 170                 175

Glu Thr Ser Ala Lys Ala Phe Ser Glu Ile Phe Thr Lys Ala Gly Val
            180                 185                 190

Asn Thr Asp Gly Lys Gly Lys Ala Trp Pro Asn Gly His Thr Asp Ser
        195                 200                 205

Ala Ala Lys Ala Glu Asp Leu Ser Thr Ala Leu Asn Arg Glu Leu Thr
    210                 215                 220

Ser Ala Glu Lys Asn Lys Val Ala Gly Leu Leu Thr Arg Thr Ile Ser
225                 230                 235                 240

Gly Gly Glu Val Val Glu Ile Arg Ala Val Ser Thr Thr Ser Val Met
                245                 250                 255

Xaa Asn Ala Cys Tyr Asp Leu Leu Ser
            260                 265

<210> SEQ ID NO 4
<211> LENGTH: 259
<212> TYPE: PRT
<213> ORGANISM: Anaplasma playts

<400> SEQUENCE: 4

Tyr Phe Tyr Val Gly Leu Asp Tyr Cys Pro Ala Phe Ser Lys Ile Asn
1               5                   10                  15

Gly Phe Glu Ile Arg Glu Ser Thr Gly Glu Thr Ala Ala Val Tyr Pro
            20                  25                  30

Tyr Met Lys Asp Gly Thr Arg Val Glu Trp Lys Ala Glu Lys Phe Asp
        35                  40                  45

Trp Asn Thr Pro Asp Pro Arg Ile Lys Phe Lys Asn Asn Pro Ile Val
    50                  55                  60

Ala Leu Glu Gly Ser Val Gly Tyr Ser Ile Gly Val Ala Arg Val Glu
65                  70                  75                  80

Leu Glu Ile Gly Tyr Glu Gln Phe Lys Thr Lys Gly Ile Arg Asp Thr
                85                  90                  95
```

```
Gly Ser Lys Glu Glu Ala Asp Ala Val Tyr Leu Leu Ala Lys Lys
            100                 105                 110

Leu Pro His Thr Leu Val Ser Asp Gln Ser Asp Lys Phe Leu Glu Glu
            115                 120                 125

Leu Lys Asn Thr Lys Ala Ala Glu Ile Val Lys Phe Ala Glu Ala Val
            130                 135                 140

Gly Thr Ser Ala Lys Asp Ile Asp Gly Lys Val Cys Lys Lys His Asn
145                 150                 155                 160

Gly Asn Ala Ala Gly Ser Trp Gln Cys Thr Gln Thr Gly Ser Glu Thr
                165                 170                 175

Ser Gly Lys Thr Leu Ser Glu Ile Phe Thr Lys Ala Gly Val Asp Ala
                180                 185                 190

Asn Gly Lys Ala Trp Pro Asn Gly Ser Asp Ala Ala Lys Ala Glu Asp
            195                 200                 205

Leu Ser Thr Ala Leu Asn Arg Glu Leu Thr Ser Ala Glu Lys Asn Lys
210                 215                 220

Val Ala Gly Leu Leu Thr Arg Thr Ile Ser Gly Glu Val Val Glu
225                 230                 235                 240

Ile Arg Ala Val Ser Thr Thr Ser Val Met Ile Asn Ala Cys Tyr Asp
                245                 250                 255

Leu Leu Ser

<210> SEQ ID NO 5
<211> LENGTH: 263
<212> TYPE: PRT
<213> ORGANISM: Anaplasma playts

<400> SEQUENCE: 5

Tyr Phe Tyr Val Gly Leu Asp Tyr Ser Pro Ala Phe Ser Lys Ile Asn
1               5                   10                  15

Gly Phe Glu Ile Arg Glu Ser Thr Gly Glu Thr Ala Ala Val Tyr Pro
            20                  25                  30

Tyr Met Lys Asp Gly Thr Arg Val Glu Trp Lys Ala Glu Lys Phe Asp
        35                  40                  45

Trp Asn Thr Pro Asp Pro Arg Ile Lys Phe Lys Asn Asn Pro Ile Val
    50                  55                  60

Ala Leu Glu Gly Ser Val Gly Tyr Ser Ile Gly Val Ala Arg Val Glu
65                  70                  75                  80

Leu Glu Ile Gly Tyr Glu Gln Phe Lys Thr Lys Gly Ile Arg Asp Thr
                85                  90                  95

Gly Ser Lys Glu Glu Ala Asp Ala Val Tyr Leu Leu Ala Lys Lys
            100                 105                 110

Leu Pro His Thr Leu Val Ser Asp Gln Ser Asp Lys Phe Leu Glu Glu
            115                 120                 125

Leu Lys Asn Thr Lys Ala Ala Glu Ile Val Lys Phe Ala Glu Ala Val
            130                 135                 140

Gly Thr Ser Ala Lys Asp Ile Asp Gly Lys Val Cys Lys Lys Asn Thr
145                 150                 155                 160

Asn Asn Ala Ala Asp Ser Trp Lys Cys Glu Gln Thr Gly Ser Gly Ser
                165                 170                 175

Asp Gly Lys Glu Phe Ser Lys Leu Phe Thr Lys Ala Gly Val Asp Ala
            180                 185                 190

Asn Glu Lys Gly Lys Ala Trp Pro Asn Gly His Thr Asp Ser Ala Ala
            195                 200                 205
```

```
Lys Ala Glu Asp Leu Ser Thr Ala Leu Asn Arg Glu Leu Thr Ser Ala
        210                 215                 220

Glu Lys Asn Lys Val Ala Gly Leu Leu Thr Arg Thr Ile Ser Gly Gly
225                 230                 235                 240

Glu Val Val Glu Ile Arg Ala Val Ser Thr Thr Ser Val Met Leu Asn
                245                 250                 255

Ala Cys Tyr Asp Leu Leu Ser
            260

<210> SEQ ID NO 6
<211> LENGTH: 22
<212> TYPE: DNA
<213> ORGANISM: Anaplasma playts

<400> SEQUENCE: 6
ccggcgttta gtaagataaa tg                                           22

<210> SEQ ID NO 7
<211> LENGTH: 21
<212> TYPE: DNA
<213> ORGANISM: Anaplasma playts

<400> SEQUENCE: 7
gcaaatttaa cgatctccgc c                                            21

<210> SEQ ID NO 8
<211> LENGTH: 26
<212> TYPE: DNA
<213> ORGANISM: Anaplasma playts

<400> SEQUENCE: 8
acagtatcgg ggtagcgaga gtagaa                                       26

<210> SEQ ID NO 9
<211> LENGTH: 27
<212> TYPE: DNA
<213> ORGANISM: Anaplasma playts

<400> SEQUENCE: 9
ggagatcggc tatgaacagt tcaagac                                      27

<210> SEQ ID NO 10
<211> LENGTH: 22
<212> TYPE: PRT
<213> ORGANISM: Anaplasma playts

<400> SEQUENCE: 10

Lys Asp Gly Thr Arg Val Glu Trp Lys Ala Glu Lys Phe Asp Trp Asn
1               5                   10                  15

Thr Pro Asp Pro Arg Ile
            20

<210> SEQ ID NO 11
<211> LENGTH: 26
<212> TYPE: PRT
<213> ORGANISM: Anaplasma playts

<400> SEQUENCE: 11

Lys Asp Gly Thr Arg Val Glu Trp Lys Ala Glu Lys Phe Asp Trp Asn
1               5                   10                  15

Thr Pro Asp Pro Arg Ile Lys Phe Lys Asn
            20                  25
```

<210> SEQ ID NO 12
<211> LENGTH: 265
<212> TYPE: PRT
<213> ORGANISM: Anaplasma playts
<220> FEATURE:
<221> NAME/KEY: MISC_FEATURE
<222> LOCATION: (9)..(9)
<223> OTHER INFORMATION: The X at position 9 can be S or C.
<220> FEATURE:
<221> NAME/KEY: MISC_FEATURE
<222> LOCATION: (153)..(153)
<223> OTHER INFORMATION: The X at position 153 can be G or K.
<220> FEATURE:
<221> NAME/KEY: MISC_FEATURE
<222> LOCATION: (159)..(159)
<223> OTHER INFORMATION: The X at position 159 can be N or H.
<220> FEATURE:
<221> NAME/KEY: MISC_FEATURE
<222> LOCATION: (160)..(160)
<223> OTHER INFORMATION: The X at position 160 can be T or N.
<220> FEATURE:
<221> NAME/KEY: MISC_FEATURE
<222> LOCATION: (161)..(161)
<223> OTHER INFORMATION: The X at position 161 can be G or N.
<220> FEATURE:
<221> NAME/KEY: MISC_FEATURE
<222> LOCATION: (165)..(165)
<223> OTHER INFORMATION: The X at position 165 can be G or N or D.
<220> FEATURE:
<221> NAME/KEY: MISC_FEATURE
<222> LOCATION: (168)..(168)
<223> OTHER INFORMATION: The X at position 168 can be K or Q.
<220> FEATURE:
<221> NAME/KEY: MISC_FEATURE
<222> LOCATION: (170)..(170)
<223> OTHER INFORMATION: The X at position 170 can be E or T.
<220> FEATURE:
<221> NAME/KEY: MISC_FEATURE
<222> LOCATION: (172)..(172)
<223> OTHER INFORMATION: The X at position 172 can be T or P.
<220> FEATURE:
<221> NAME/KEY: MISC_FEATURE
<222> LOCATION: (175)..(175)
<223> OTHER INFORMATION: The X at position 175 can be G or E.
<220> FEATURE:
<221> NAME/KEY: MISC_FEATURE
<222> LOCATION: (176)..(176)
<223> OTHER INFORMATION: The X at position 176 can be S or T.
<220> FEATURE:
<221> NAME/KEY: MISC_FEATURE
<222> LOCATION: (177)..(177)
<223> OTHER INFORMATION: The X at position 177 can be D or E or S.
<220> FEATURE:
<221> NAME/KEY: MISC_FEATURE
<222> LOCATION: (178)..(178)
<223> OTHER INFORMATION: The X at position 178 can be T or absent.
<220> FEATURE:
<221> NAME/KEY: MISC_FEATURE
<222> LOCATION: (179)..(179)
<223> OTHER INFORMATION: The X at position 179 can be S or absent.
<220> FEATURE:
<221> NAME/KEY: MISC_FEATURE
<222> LOCATION: (180)..(180)
<223> OTHER INFORMATION: The X at position 180 can be G or A.
<220> FEATURE:
<221> NAME/KEY: MISC_FEATURE
<222> LOCATION: (182)..(182)
<223> OTHER INFORMATION: The X at position 182 can be E or A or T.
<220> FEATURE:
<221> NAME/KEY: MISC_FEATURE
<222> LOCATION: (183)..(183)
<223> OTHER INFORMATION: The X at position 183 can be F or L.
<220> FEATURE:
<221> NAME/KEY: MISC_FEATURE
<222> LOCATION: (185)..(185)
<223> OTHER INFORMATION: The X at position 185 can be K or E.
<220> FEATURE:

```
<221> NAME/KEY: MISC_FEATURE
<222> LOCATION: (186)..(186)
<223> OTHER INFORMATION: The X at position 186 can be L or I.
<220> FEATURE:
<221> NAME/KEY: MISC_FEATURE
<222> LOCATION: (193)..(193)
<223> OTHER INFORMATION: The X at position 193 can be D or N.
<220> FEATURE:
<221> NAME/KEY: MISC_FEATURE
<222> LOCATION: (194)..(194)
<223> OTHER INFORMATION: The X at position 194 can be A or T.
<220> FEATURE:
<221> NAME/KEY: MISC_FEATURE
<222> LOCATION: (195)..(195)
<223> OTHER INFORMATION: The X at position 195 can be N or D.
<220> FEATURE:
<221> NAME/KEY: MISC_FEATURE
<222> LOCATION: (196)..(196)
<223> OTHER INFORMATION: The X at position 196 can be E or G or absent.
<220> FEATURE:
<221> NAME/KEY: MISC_FEATURE
<222> LOCATION: (197)..(197)
<223> OTHER INFORMATION: The X at position 197 can be K or absent.
<220> FEATURE:
<221> NAME/KEY: MISC_FEATURE
<222> LOCATION: (205)..(205)
<223> OTHER INFORMATION: The X at position 205 can be H or S.
<220> FEATURE:
<221> NAME/KEY: MISC_FEATURE
<222> LOCATION: (206)..(206)
<223> OTHER INFORMATION: The X at position 206 can be T or absent.
<220> FEATURE:
<221> NAME/KEY: MISC_FEATURE
<222> LOCATION: (207)..(207)
<223> OTHER INFORMATION: The X at position 207 can be D or absent.
<220> FEATURE:
<221> NAME/KEY: MISC_FEATURE
<222> LOCATION: (208)..(208)
<223> OTHER INFORMATION: The X at position 208 can be D or S.
<220> FEATURE:
<221> NAME/KEY: MISC_FEATURE
<222> LOCATION: (257)..(257)
<223> OTHER INFORMATION: The X at position 257 can be L or I.

<400> SEQUENCE: 12

Tyr Phe Tyr Val Gly Leu Asp Tyr Xaa Pro Ala Phe Ser Lys Ile Asn
1               5                   10                  15

Gly Phe Glu Ile Arg Glu Ser Thr Gly Glu Thr Ala Ala Val Tyr Pro
            20                  25                  30

Tyr Met Lys Asp Gly Thr Arg Val Glu Trp Lys Ala Gly Lys Phe Asp
        35                  40                  45

Trp Asn Thr Pro Asp Pro Arg Ile Lys Phe Lys Asn Asn Pro Ile Val
50                  55                  60

Ala Leu Glu Gly Ser Val Gly Tyr Ser Ile Gly Val Ala Arg Val Glu
65                  70                  75                  80

Leu Glu Ile Gly Tyr Glu Gln Phe Lys Thr Lys Gly Ile Arg Asp Thr
                85                  90                  95

Gly Ser Lys Glu Glu Glu Ala Asp Ala Val Tyr Leu Leu Ala Lys Lys
            100                 105                 110

Leu Pro His Thr Leu Val Ser Asp Gln Ser Asp Lys Phe Leu Glu Glu
        115                 120                 125

Leu Lys Asn Thr Lys Ala Ala Glu Ile Val Lys Phe Ala Glu Ala Val
130                 135                 140

Gly Thr Ser Ala Lys Asp Ile Asp Xaa Lys Val Cys Lys Lys Xaa Xaa
145                 150                 155                 160

Xaa Asn Ala Ala Xaa Ser Trp Xaa Cys Xaa Gln Xaa Gly Ser Xaa Xaa
                165                 170                 175
```

Xaa Xaa Xaa Xaa Lys Xaa Xaa Ser Xaa Xaa Phe Thr Lys Ala Gly Val
            180                 185                 190

Xaa Xaa Xaa Xaa Xaa Gly Lys Ala Trp Pro Asn Gly Xaa Xaa Xaa Xaa
            195                 200                 205

Ala Ala Lys Ala Glu Asp Leu Ser Thr Ala Leu Asn Arg Glu Leu Thr
            210                 215                 220

Ser Ala Glu Lys Asn Lys Val Ala Gly Leu Leu Thr Arg Thr Ile Ser
225                 230                 235                 240

Gly Gly Glu Val Val Glu Ile Arg Ala Val Ser Thr Thr Ser Val Met
            245                 250                 255

Xaa Asn Ala Cys Tyr Asp Leu Leu Ser
            260                 265

<210> SEQ ID NO 13
<211> LENGTH: 28
<212> TYPE: PRT
<213> ORGANISM: Anaplasma playts

<400> SEQUENCE: 13

Arg Val Glu Leu Glu Ile Gly Tyr Glu Gln Phe Lys Thr Lys Gly Ile
1               5                   10                  15

Arg Asp Thr Gly Ser Lys Glu Glu Ala Asp Ala
            20                  25

<210> SEQ ID NO 14
<211> LENGTH: 27
<212> TYPE: PRT
<213> ORGANISM: Anaplasma playts

<400> SEQUENCE: 14

Cys Lys Asp Gly Thr Arg Val Glu Trp Lys Ala Glu Lys Phe Asp Trp
1               5                   10                  15

Asn Thr Pro Asp Pro Arg Ile Lys Pro Lys Asn
            20                  25

<210> SEQ ID NO 15
<211> LENGTH: 23
<212> TYPE: PRT
<213> ORGANISM: Anaplasma playts

<400> SEQUENCE: 15

Cys Lys Asp Gly Thr Arg Val Glu Trp Lys Ala Glu Lys Phe Asp Trp
1               5                   10                  15

Asn Thr Pro Asp Pro Arg Ile
            20

<210> SEQ ID NO 16
<211> LENGTH: 795
<212> TYPE: DNA
<213> ORGANISM: Anaplasma playts

<400> SEQUENCE: 16
tatttttatg ttggtytgga ytatwgcccg gcgtttagta agataaatgg gtttgagata      60
agagagagta ccggggaaac tgcggcagta tatccgtaca tgaaagatgg aactagagtg     120
gagtggaaag ctgagaagtt cgactggaac acaccagatc cgaggattaa gtttaaaaac     180
aatcctatcg tagcgttgga aggaagtgtg ggctacagta tcggggtagc gagagtagaa     240
ctggagatcg gctatgaaca gttcaagacg aaaggaataa gatacggg aagtaaggaa       300 gaagaagctg atgccgtgta cctgttggct aagaagctac cgcataccct ggtgagtgac     360

```
cagagcgata aattcctgga ggagctgaag aatacgaaag cggcggagat cgttaaattt      420
gctgaggctg ttggcacatc ggcaaaggat attgataaga aggtttgtaa gaagcacact      480
aacaatgcgg cgaacagttg gaagtgcgag cagcctggaa gcggcaccga gacaagcgcc      540
aaggcgttca gtgaaatatt tacgaaggca ggcgtaaata ctgacggcaa aggcaaagca      600
tggcctaacg ggcacaccga cagcgccgcg aaagcggaag acctaagtac ggcgttgaat      660
agagaactaa ccagcgccga aaagaacaag gtagctgggc tgctaaccag gactatatcc      720
ggtggtgagg tagtggagat ccgtgcggtg tcgacaacgt cagtaatgwt aaatgcgtgy      780
tacgatctgc tgagc                                                      795

<210> SEQ ID NO 17
<211> LENGTH: 777
<212> TYPE: DNA
<213> ORGANISM: Anaplasma playts

<400> SEQUENCE: 17 tattttatg ttggtttgga ttattgcccg gcgtttagta agataaatgg gtttgagata       60
agagagagta ccggggaaac tgcggcagta tatccgtaca tgaaagatgg aactagagtg      120
gagtggaaag ctgagaagtt cgactggaac acaccagatc cgaggattaa gtttaaaaac      180
aatcctatcg tagcgttaga aggaagtgtg ggctacagta tcggggtagc gagagtagaa      240
ctggagatcg gctatgaaca gttcaagacg aaaggaataa gagatacggg aagtaaggaa      300
gaagaagctg atgccgtgta cctgttggct aagaagctac cgcatacccct ggtgagtgac     360 cagagcgata aattcctgga ggagctgaag aatacgaaag cggcggagat cgttaagttt      420
gctgaggctg ttggcacatc ggcaaaggat attgatgaa aggtttgtaa gaagcacaac      480
ggcaatgcgg caggcagttg gcagtgcacg cagactggca gcgaaacaag cggcaagacg      540
ttgagtgaga tatttacgaa ggctggcgtg gatgctaacg gcaaagcatg gcctaacgga      600
agcgacgccg cgaaagcgga agacctaagt actgcgttga atagagaact aaccagcgct      660
gaaaagaaca aggtagctgg cctactaacc aggactatat ccggtggcga ggtagtggag      720
atccgtgcgg tgtcgacaac gtcagtaatg ataaacgcat gttacgatct gctgagc       777

<210> SEQ ID NO 18
<211> LENGTH: 789
<212> TYPE: DNA
<213> ORGANISM: Anaplasma playts

<400> SEQUENCE: 18 tattttatg ttggtttaga ttatagtccg gcgtttagta agataaatgg gtttgagata       60
agagagagta ccggggaaac tgcggcagta tatccgtaca tgaaagatgg aactagagtg      120
gagtggaaag ctgagaagtt cgactggaac acaccagatc cgaggattaa gtttaaaaac      180
aatcctatcg tagcgttgga aggaagtgtg ggctacagta tcggggtagc gagagtagaa      240
ctggagatcg gctatgaaca gttcaagacg aaaggaataa gagatacggg aagtaaggaa      300
gaagaagctg atgccgtgta cctgttggct aagaagctac cgcatacccct ggtgagtgac     360 cagagcgata aattcctgga ggagctgaag aatacgaaag cggcggagat cgttaaattt      420
gctgaggctg ttggcacatc ggcaaaggat attgatggaa aggtttgtaa gaagaacact     480
aacaatgcgg cagacagttg gaagtgcgag cagactggca gcggcagcga cggcaaggag     540
ttcagtaaac tatttacgaa ggctggcgtg gatgctaacg agaaaggcaa agcgtggcct      600
```

-continued

```
aacgggcaca ccgacagcgc cgcgaaagcg gaagacctaa gtacggcgtt gaatagagaa    660
ctaaccagcg ccgaaaagaa caaggtagct gggctgctaa ccaggactat atccggtggt    720
gaggtagtgg agatccgtgc ggtgtcgaca acgtcagtaa tgttaaacgc ctgctacgat    780
ctgctgagc                                                            789
```

<210> SEQ ID NO 19
<211> LENGTH: 293
<212> TYPE: PRT
<213> ORGANISM: Anaplasma phagocytophilum

<400> SEQUENCE: 19

```
Tyr Phe Tyr Val Gly Leu Asp Tyr Ser Pro Ala Phe Ser Lys Ile Arg
1               5                   10                  15

Asp Phe Ser Ile Arg Glu Ser Asn Gly Glu Thr Lys Ala Val Tyr Pro
            20                  25                  30

Tyr Leu Lys Asp Gly Lys Ser Val Lys Leu Glu Ser His Lys Phe Asp
        35                  40                  45

Trp Asn Thr Pro Asp Pro Arg Ile Gly Phe Lys Asp Asn Met Leu Val
    50                  55                  60

Ala Met Glu Gly Ser Val Gly Tyr Gly Ile Gly Gly Ala Arg Val Glu
65                  70                  75                  80

Leu Glu Ile Gly Tyr Glu Arg Phe Lys Thr Lys Gly Ile Arg Asp Ser
                85                  90                  95

Gly Ser Lys Glu Asp Glu Ala Asp Thr Val Tyr Leu Leu Ala Lys Glu
            100                 105                 110

Leu Ala Tyr Asp Val Val Thr Gly Gln Thr Asp Asn Leu Ala Ala Ala
        115                 120                 125

Leu Ala Lys Thr Ser Gly Lys Asp Ile Val Gln Phe Ala Lys Ala Val
    130                 135                 140

Glu Ile Ser Tyr Pro Ser Ile Asp Gly Lys Val Cys Ser Gly Lys His
145                 150                 155                 160

Ala Ala Leu Ala Ala Asn Thr Asn Ala Glu Lys Lys Tyr Ala Val Glu
                165                 170                 175

Pro Ala Asn Gly Gly Thr Asp Gly Ser Thr Ser Gln Cys Ser Gly Leu
            180                 185                 190

Ser Asn Gly Ser Ala Glu Ala Ala His Lys Tyr Leu Ser Lys Phe Val
        195                 200                 205

Ser Leu Thr Gly Val Val Glu Gly Lys Asn Trp Pro Thr Gly Arg Ser
    210                 215                 220

Ser Asn Ser Asn Ser Ile Val Val Gly Ala Pro Asn Ser Asn Ala
225                 230                 235                 240

Asn Ala Met Ala Lys Asp Leu Val Lys Glu Leu Thr Pro Glu Glu Lys
                245                 250                 255

Thr Ile Val Ala Gly Leu Leu Ala Lys Thr Ile Glu Gly Gly Glu Val
            260                 265                 270

Val Glu Ile Arg Ala Val Ser Ser Thr Ser Val Met Val Asn Ala Cys
        275                 280                 285

Tyr Asp Leu Leu Ser
    290
```